US011845111B2

(12) United States Patent
Semans

(10) Patent No.: US 11,845,111 B2
(45) Date of Patent: *Dec. 19, 2023

(54) COUNTERTOP APPARATUS FOR WASHING ARTICLES

(71) Applicant: Hillsborough Bay Group, LLC, Tampa, FL (US)

(72) Inventor: Ellen Semans, Tampa, FL (US)

(73) Assignee: Hillsborough Bay Group, LLC, Tampa, FL (US)

( * ) Notice: Subject to any disclaimer, the term of this patent is extended or adjusted under 35 U.S.C. 154(b) by 53 days.

This patent is subject to a terminal disclaimer.

(21) Appl. No.: 17/520,807

(22) Filed: Nov. 8, 2021

(65) Prior Publication Data

US 2022/0055072 A1 Feb. 24, 2022

Related U.S. Application Data

(63) Continuation of application No. 16/717,140, filed on Dec. 17, 2019, now Pat. No. 11,167,323, which is a
(Continued)

(51) Int. Cl.
*B08B 3/02* (2006.01)
*B08B 3/10* (2006.01)
(Continued)

(52) U.S. Cl.
CPC .............. *B08B 3/02* (2013.01); *A61M 1/062* (2014.02); *B08B 3/10* (2013.01); *A61J 1/00* (2013.01);
(Continued)

(58) Field of Classification Search
CPC ....... B08B 3/02; B08B 3/10; B08B 2203/007; A61M 1/062; A61M 2209/10; A61J 9/00; A61J 11/00
(Continued)

(56) References Cited

U.S. PATENT DOCUMENTS 2,065,466 A * 12/1936 Horn ...................... B08B 9/0839
134/102.1
RE22,832 E * 1/1947 Meyerson ................. A61L 2/00
422/26
(Continued)

FOREIGN PATENT DOCUMENTS

DE 4438279 A 5/1996
GB 2134788 A * 8/1984 ............... A61L 2/07
(Continued)

*Primary Examiner* — David G Cormier
*Assistant Examiner* — Thomas Bucci
(74) *Attorney, Agent, or Firm* — GrayRobinson, P.A.; Michael J. Colitz, III

(57) ABSTRACT

Disclosed is a portable and self-contained washing and sanitizing apparatus. The apparatus finds particular application in washing small baby items such as bottles, nipples, teething rings or toys. However, the apparatus can likewise be used to clean dishware, glassware, or utensils. The apparatus includes a container with a lid, the container housing the items to be washed; an accessory holder connected to the lid for holding accessories during washing operations; a water reservoir for storing and collecting wash water; and a housing for interconnecting the container and reservoir.

12 Claims, 25 Drawing Sheets

Related U.S. Application Data continuation of application No. 15/727,874, filed on Oct. 9, 2017, now Pat. No. 10,507,497, which is a continuation-in-part of application No. 14/099,322, filed on Dec. 6, 2013, now Pat. No. 9,782,803, which is a continuation-in-part of application No. 13/466,300, filed on May 8, 2012, now abandoned, which is a continuation-in-part of application No. 12/703,410, filed on Feb. 10, 2010, now Pat. No. 8,388,765.

(51) Int. Cl.
*A61M 1/06* (2006.01)
*A61J 9/00* (2006.01)
*A61J 1/00* (2023.01)

(52) U.S. Cl.
CPC ............ *A61J 9/00* (2013.01); *A61M 2209/10* (2013.01); *B08B 2203/007* (2013.01)

(58) Field of Classification Search
USPC .......................................................... 134/34
See application file for complete search history.

(56) References Cited

U.S. PATENT DOCUMENTS

| | | | |
|---|---|---|---|
| 2,484,681 A * | 10/1949 | Brewster | A61L 2/06 422/303 |
| 2,877,778 A * | 3/1959 | Kirby | A47L 15/06 134/107 |
| 2,955,674 A | 10/1960 | Krammes | |
| 3,078,861 A * | 2/1963 | Miller | B08B 9/28 134/96.1 |
| 3,114,375 A | 12/1963 | Blanchard | |
| 3,406,696 A | 10/1968 | MacChesney et al. | |
| 4,157,922 A | 6/1979 | Luik | |
| 4,560,455 A * | 12/1985 | Porta | A01N 59/00 210/756 |
| 5,143,101 A | 9/1992 | Mor | |
| 5,161,559 A | 11/1992 | Yoshihara et al. | |
| 5,209,784 A | 5/1993 | Bellman | |
| 5,522,410 A * | 6/1996 | Meilleur | A47L 15/0065 134/108 |
| 6,080,361 A | 6/2000 | Borovsky | |
| 6,338,350 B1 | 1/2002 | Ewen | |
| 6,390,104 B1 | 5/2002 | Gagnon | |
| 6,932,094 B2 | 8/2005 | Chen et al. | |
| 7,165,562 B2 * | 1/2007 | Myong | B08B 3/02 134/169 R |
| 7,478,642 B2 | 1/2009 | Koch et al. | |
| 8,388,765 B2 | 3/2013 | Semans | |
| 9,782,803 B2 * | 10/2017 | Semans | B08B 3/04 |
| 2003/0079761 A1 | 5/2003 | Rich | |
| 2003/0188769 A1 * | 10/2003 | Eisenberg | B08B 9/28 134/152 |
| 2004/0123885 A1 | 7/2004 | Myong | |
| 2006/0065666 A1 | 3/2006 | Dunn et al. | |
| 2007/0277855 A1 | 12/2007 | DiPanni | |
| 2008/0099055 A1 * | 5/2008 | Lemley | A47L 15/502 134/33 |
| 2009/0101185 A1 | 4/2009 | Pardini | |
| 2009/0242000 A1 | 10/2009 | Jimenez | |
| 2010/0043829 A1 | 2/2010 | Kim et al. | |
| 2011/0192431 A1 | 8/2011 | Semans | |
| 2012/0216838 A1 | 8/2012 | Semans et al. | |

FOREIGN PATENT DOCUMENTS

| | | | | |
|---|---|---|---|---|
| GB | 2260483 A * | 4/1993 | ......... | A47L 15/0065 |
| GB | 2260483 A | 4/1993 | | |

* cited by examiner

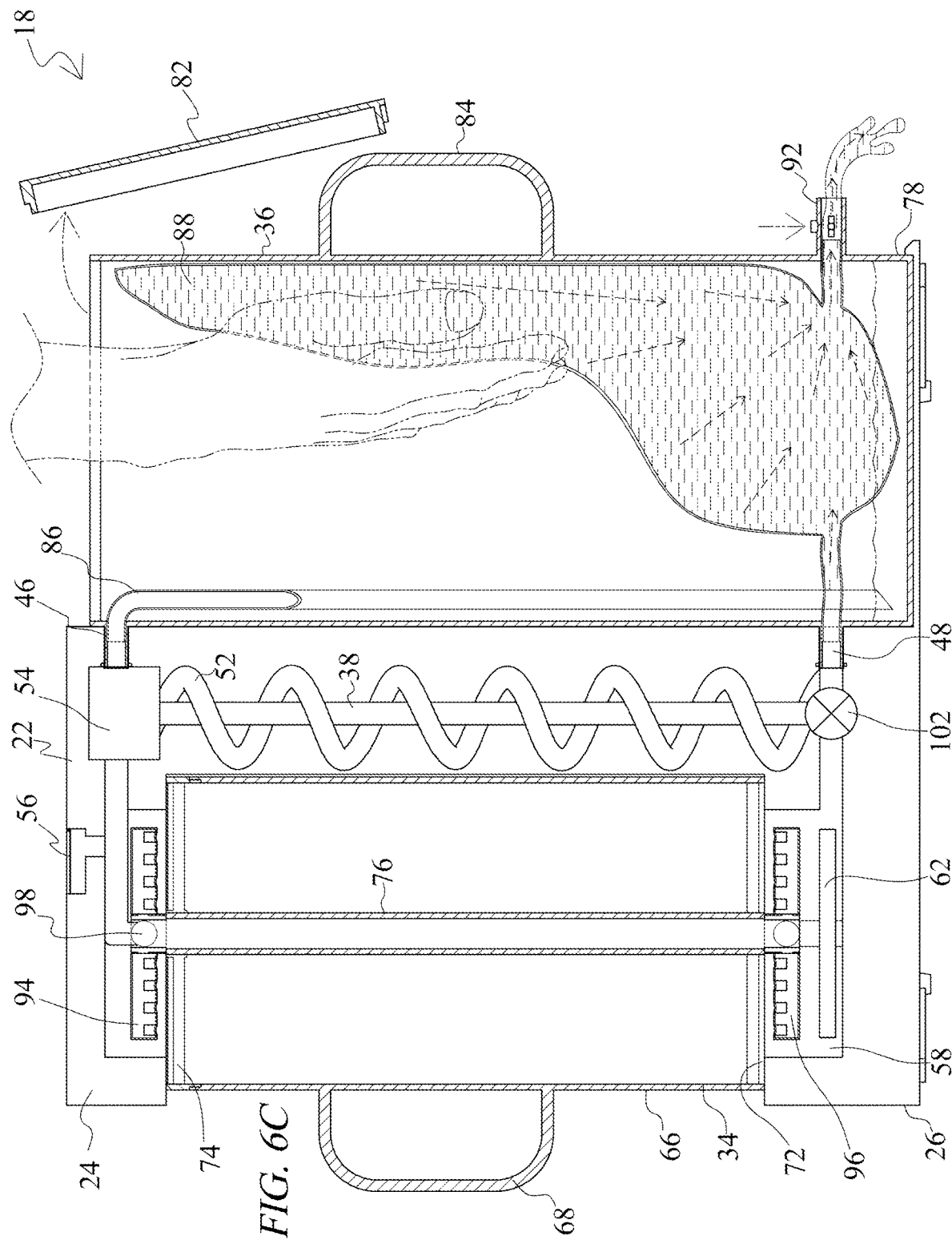

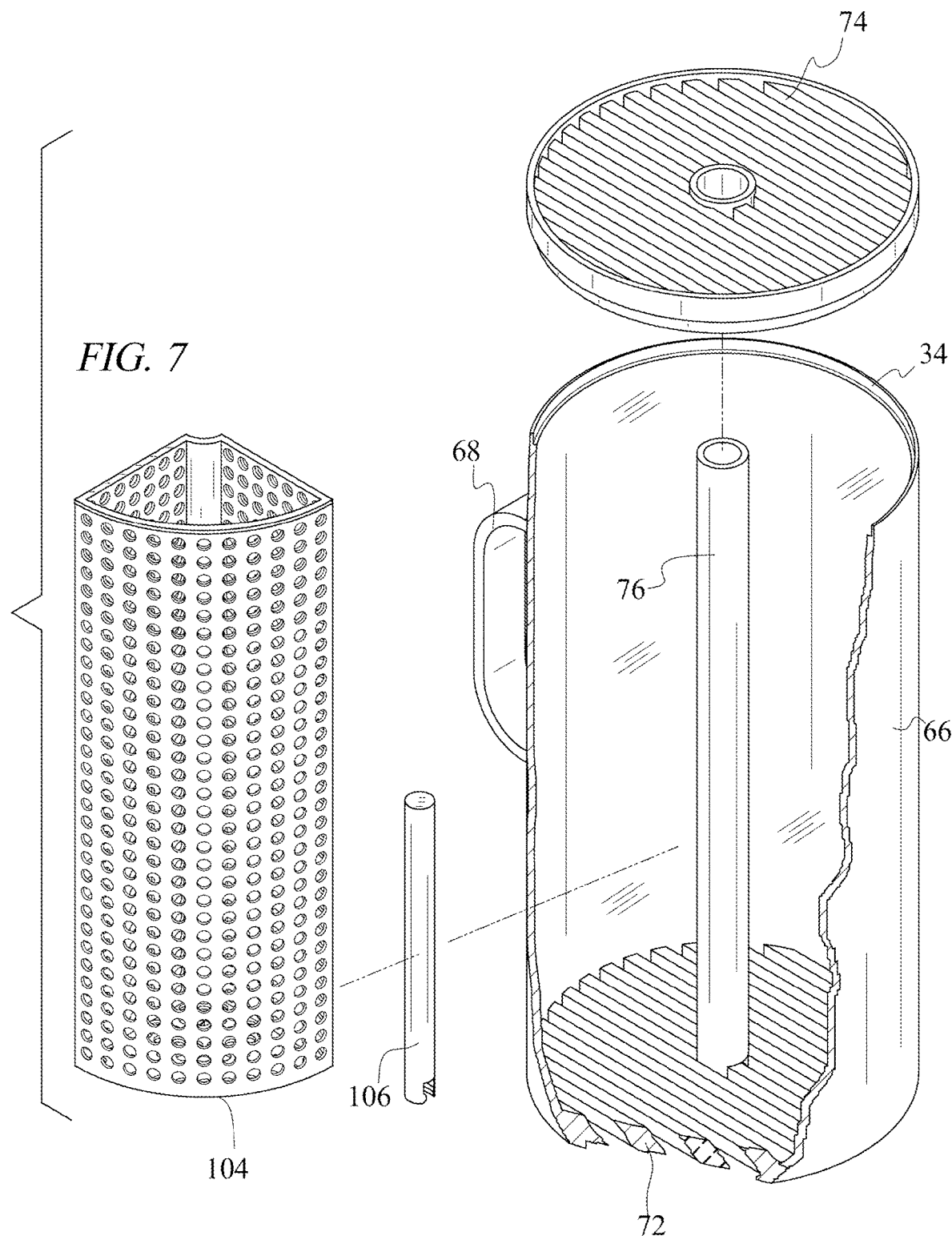

COUNTERTOP APPARATUS FOR WASHING ARTICLES

RELATED APPLICATION DATA

This application is a continuation of and claims priority to co-pending application Ser. No. 16/717,140, filed Dec. 17, 2019, and entitled "Apparatus and Method for Washing and Sanitizing Articles for an Infant," now U.S. Pat. No. 11,167,323, issued Nov. 9, 2021, which is a continuation of and claims priority to application Ser. No. 15/727,874, filed Oct. 9, 2017, and entitled "Apparatus and Method for Washing and Sanitizing Articles for an Infant," now U.S. Pat. No. 10,507,497, issued Dec. 17, 2019, which is a continuation-in-part of and claims priority to application Ser. No. 14/099,322 filed Dec. 6, 2013, and entitled "Apparatus for Washing and Sanitizing Articles for an Infant," now U.S. Pat. No. 9,782,803 issued Oct. 10, 2017, which is a continuation-in-part of application Ser. No. 13/466,300 filed on May 8, 2012 and entitled "Method for Washing and Sanitizing Articles for an Infant," which is a continuation-in-part of application Ser. No. 12/703,410 filed on Feb. 10, 2010 and entitled "Apparatus for Washing and Sanitizing Articles for an Infant," now U.S. Pat. No. 8,388,765 issued Mar. 5, 2013. The contents of these applications are fully incorporated herein for all purposes.

TECHNICAL FIELD

This disclosure relates to a portable washing apparatus, and more particularly, to a countertop apparatus and method for use in washing articles.

BACKGROUND OF THE INVENTION

Washing dishware, glassware, and utensils by hand can be a chore. Dishwashers, of course, greatly assist with this task and are ubiquitous in most modern kitchens. The drawback of dishwashers is that most are large and designed to clean a full load of dishes, glassware, and utensils. In order to complete a single wash cycle, they require large amounts to water, detergent, energy, and time. This is a significant drawback when cleaning only a few items. For example, individuals living alone may only need to wash a few items at a time. These individuals may be elderly people living in retirement homes or college aged individuals living in a dorm. These individuals generally do not have a need for large dishwashers. Instead, they have a need for a smaller washing apparatus that is designed to wash only a few items and that can reside on a countertop.

Life with a small child also involves the repeated cleaning of a small number of articles. These articles can include, for example, baby bottles, bottle liners, nipples, nipple rings, sippy cups, teething devices, and toys. Each of these articles must be repeatedly cleaned to avoid the spread of germs and bacteria to the child and caregiver. Many times this involves hand washing the articles. Hand washing, however, is time consuming, requires large volumes of water, and requires the care giver to direct his or her attention away from the child. Cleaning these articles in a conventional dishwasher is wasteful as typically only a few articles need to be cleaned at any one given time.

Thus, there exists a need in the art for a dedicated appliance for the convenient washing of only a few items. These items can be dishware, glassware, or utensils, or infant articles, such as baby bottles and associated accoutrements. There also exists a need in the art for a small appliance that does not need to be coupled to an external source of water and which can be used on a countertop. The present invention substantially fulfills this need.

SUMMARY OF THE INVENTION

It is therefore one of the objectives of this disclosure is to provide a small appliance that can wash a few items at a time.

It is another objective of this disclosure to provide an apparatus that is specifically adapted to wash infant articles such as baby bottles.

It is another object of this invention to provide an apparatus that is self-contained and does not need an external water supply.

It is a further object of the present invention to provide a portable washing apparatus that can store a wide variety of articles and that can properly orient the articles for cleaning.

It is a further object of this invention to provide a washing apparatus that can carry out a number of distinct washing cycles, such as a steam cycle, a detergent cycle, a rinse cycle, and a heating cycle.

It is yet another object of this invention to provide a portable, countertop appliance that can efficiently and effectively clean smaller kitchen items.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 6C is a sectional view showing the fluid being evacuated from the collection bag of the reservoir.

FIG. 7 is a partially exploded view of the container and basket.

Similar reference characters refer to similar parts throughout the several views of the drawings.

PARTS LIST

| | |
|---|---|
| 300 | Apparatus |
| 302 | Housing |
| 304 | Control Panel |
| 308 | Fluid Chamber |
| 310 | Water Filter |
| 312 | Rinse Water Container |
| 314 | Level Indicator |
| 316 | Water Outlet Port |
| 317 | Lower Supply Port |
| 318 | Filter Container |
| 319 | Internal Water Line |
| 320 | Detergent Basket |
| 321 | Internal Recirculation Line |
| 322 | Jet Sprayer |
| 324 | Center Jet Sprayer |
| 326 | First Lid |
| 328 | Opening in Housing |
| 332 | Washing Chamber |
| 334 | Bottle |
| 338 | Grid |
| 342 | Jet Sprayer Manifold |
| 344 | In-line Heater |
| 346 | Rounded Holders |
| 350 | Second Lid |
| 352 | Accessory Holder |
| 353 | Frame |
| 354 | Surface Portion |
| 355 | Openings |
| 356 | Nipples |
| 357 | Central Cavity |
| 358 | Protrusions |
| 362 | Pump |
| 368 | First Solenoid Valve |
| 370 | Second Solenoid Valve |
| 372 | Third Solenoid Valve |
| 373 | Detergent Line |
| 382 | Recirculation Inlet Port |
| 384 | Waste Water Outlet Port |
| 392 | Waste Water Container |

PARTS LIST

| | |
|---|---|
| 394 | Waste Water Inlet Port |
| 396 | Drain Port |
| 402 | Breast Pump Assembly |
| 404 | Breast Pump Shield |
| 406 | Breast Pump Membrane |
| 408 | Breast Pump Bottle |
| 410 | Breast Pump Connector |
| 412 | Breast Pump Tubing |
| 414 | End of Breast Pump Tubing |

DETAILED DESCRIPTION OF THE PREFERRED EMBODIMENTS

The present invention relates to a portable and self-contained washing apparatus. The apparatus finds particular application in washing small baby items such as bottles, nipples, teething rings or toys. However, the apparatus can likewise be used to clean dishware, glassware, or utensils. The apparatus includes three primary components: a container for housing the items to be washed; a water reservoir for storing and collecting wash water; and a housing for interconnecting the container and reservoir. Details regarding the various components of the present invention, and the manner in which they interrelate, will be described in greater detail hereinafter.

Figure 1:
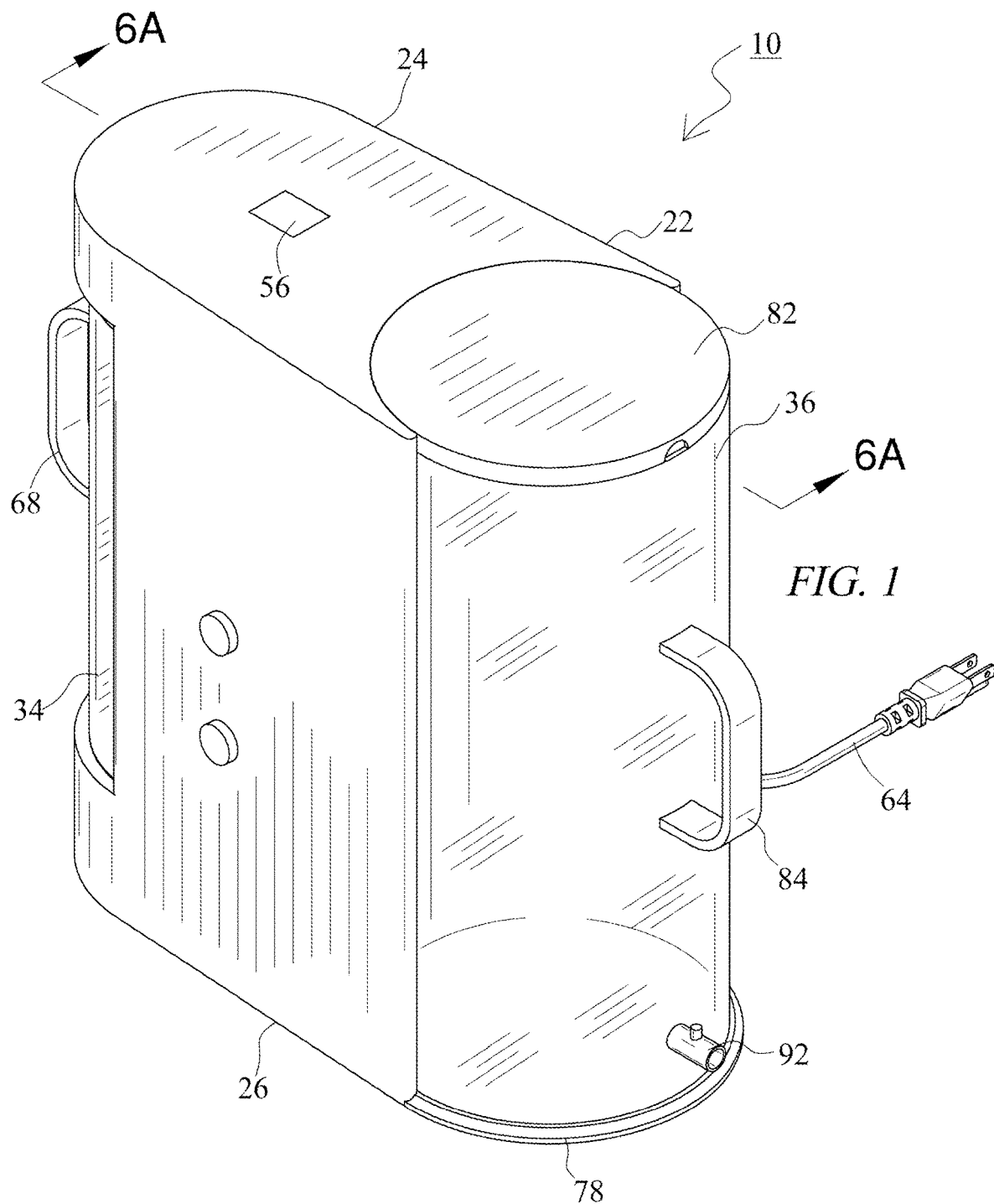
FIG. 1 is a perspective view of the apparatus of the present invention.
Figure 2:
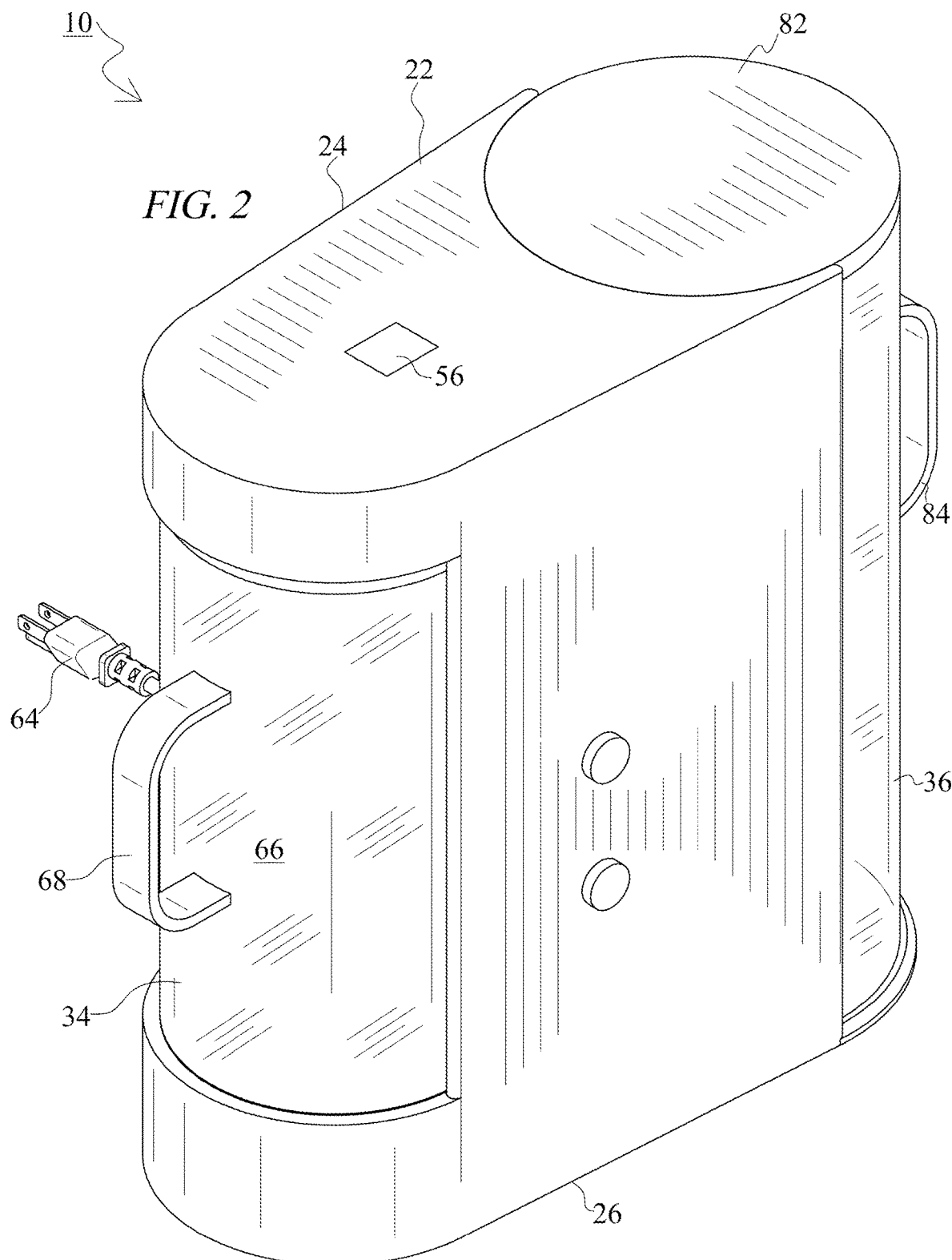
FIG. 2 is an additional perspective view of the apparatus of the present invention.
Figure 3:
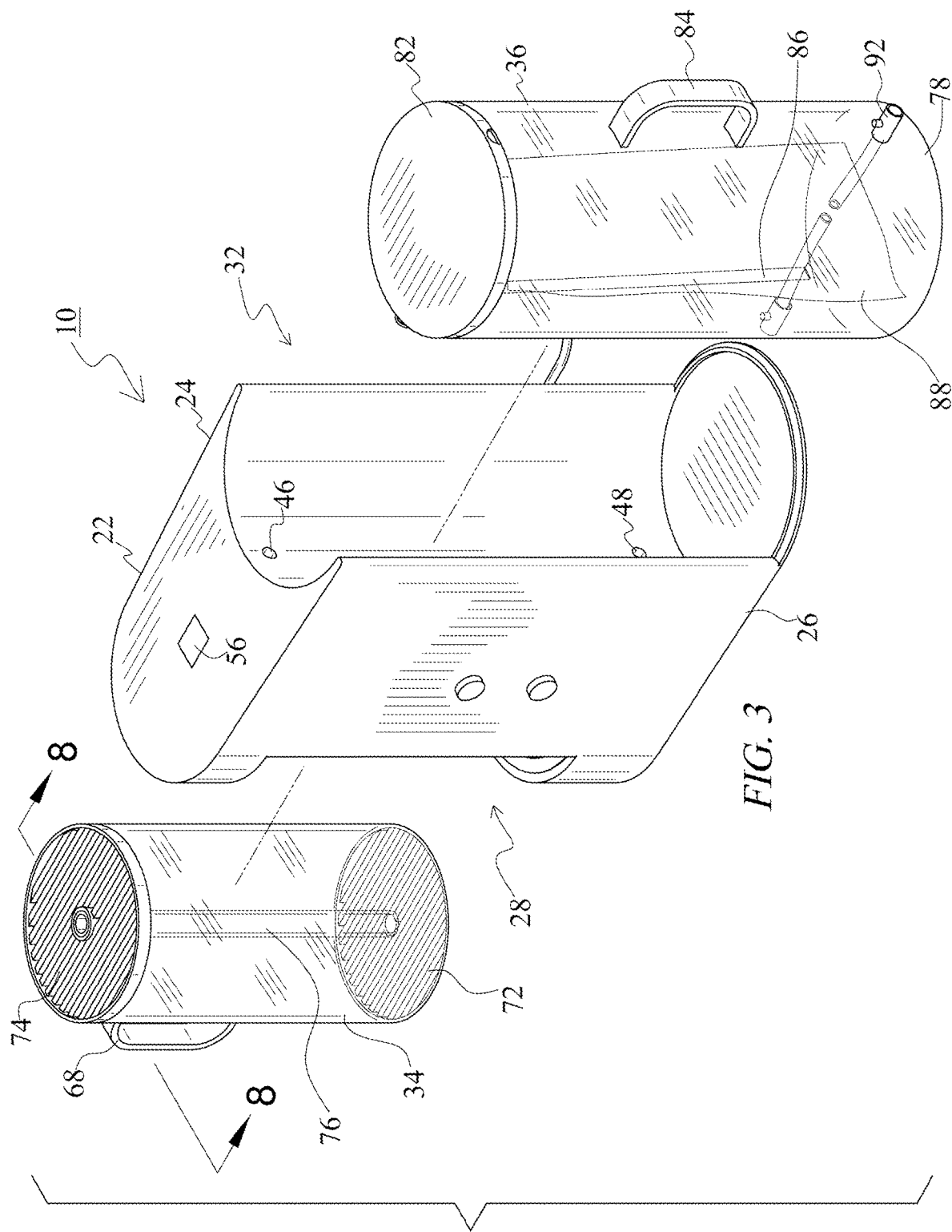
FIG. 3 is a partially exploded view of the apparatus of the present invention showing the container and reservoir separated from the base.
Figure 4:
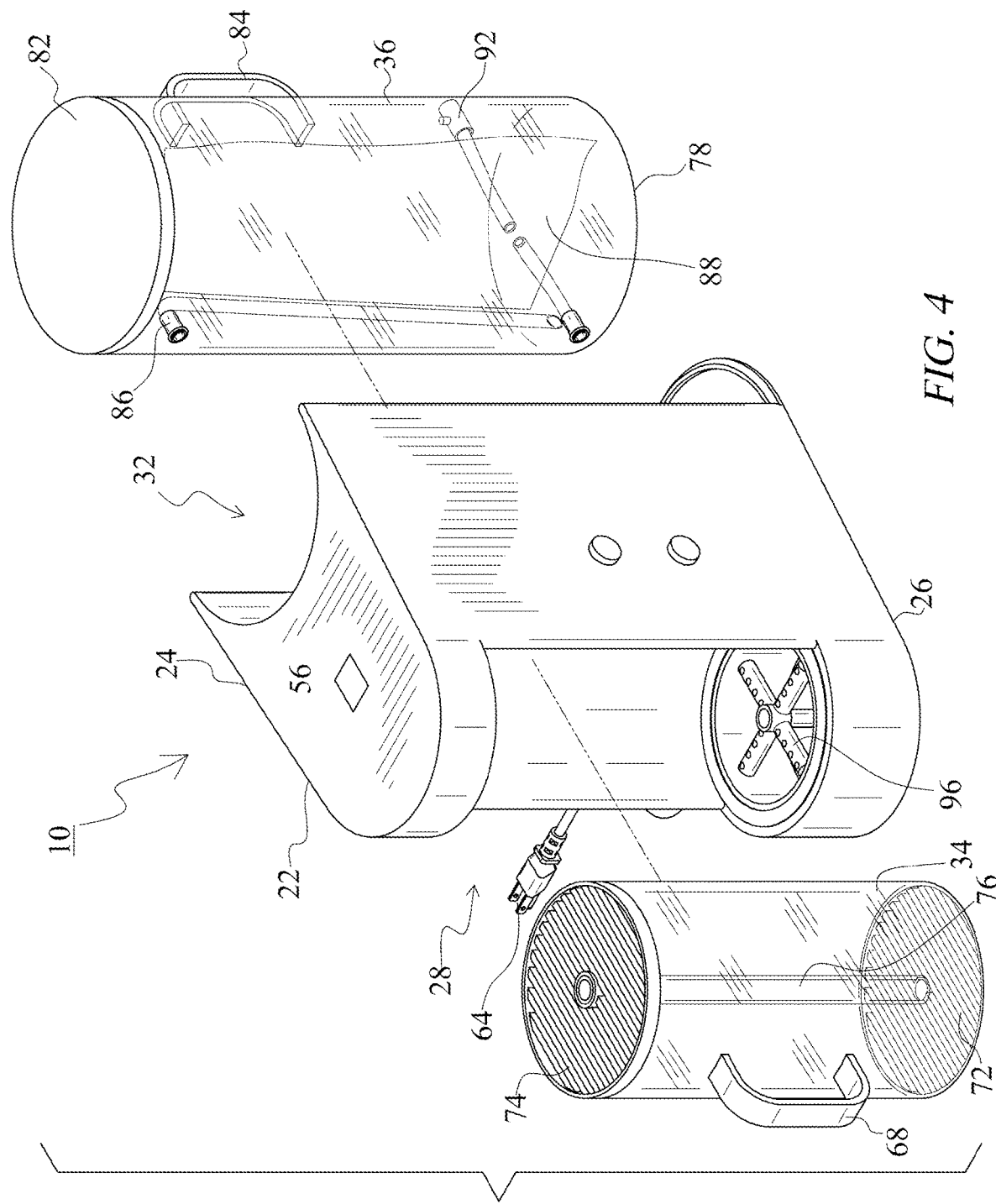
FIG. 4 is a partially exploded view of the apparatus of the present invention showing the container and reservoir separated from the base.
Figure 5:
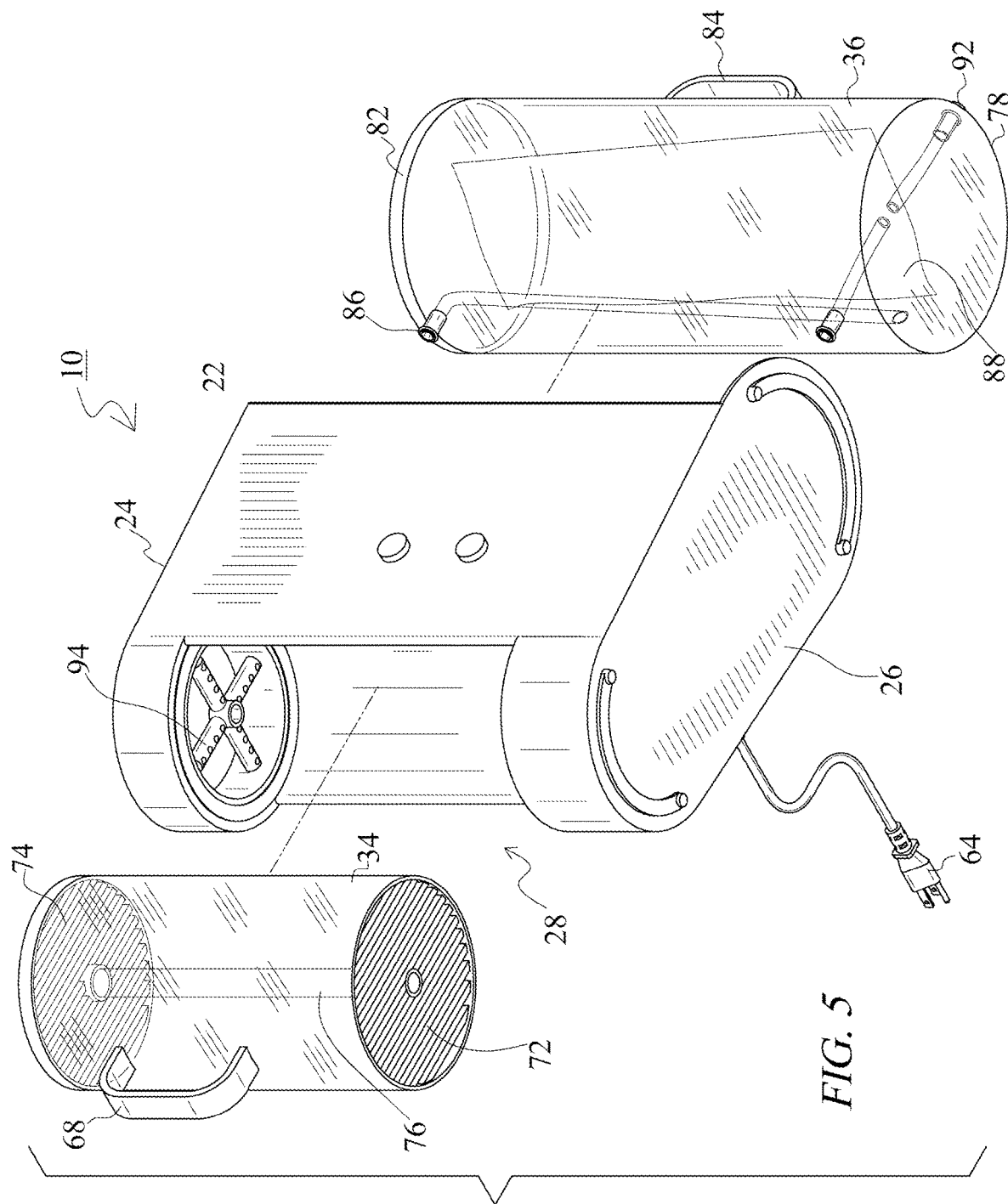
FIG. 5 is another partially exploded view of the apparatus of the present invention showing the container and reservoir separated from the base.
Figure 6A:
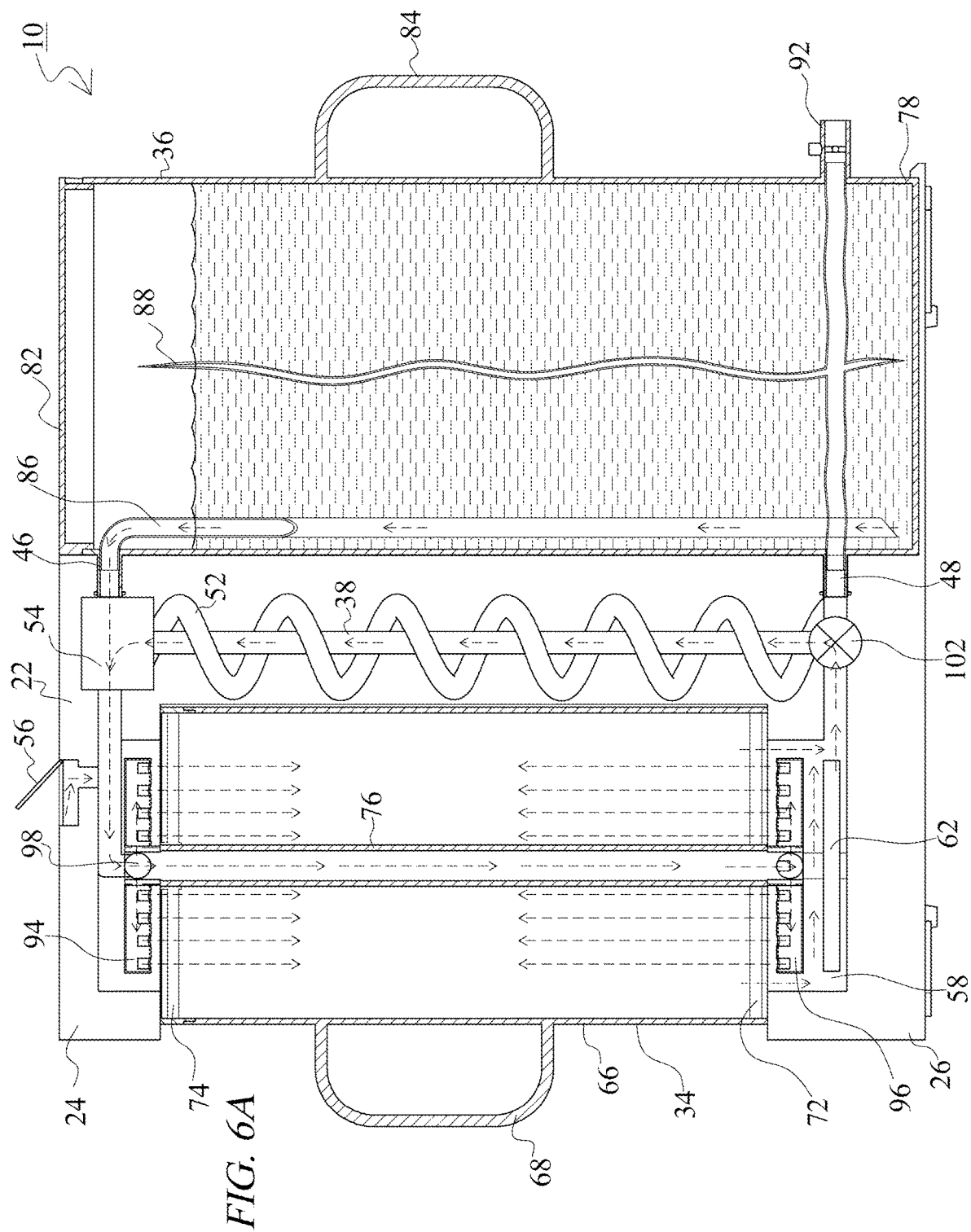
FIG. 6A is a sectional view taken along line 6A-6A from FIG. 1 and showing the reservoir filled with fluid.
Figure 6B:
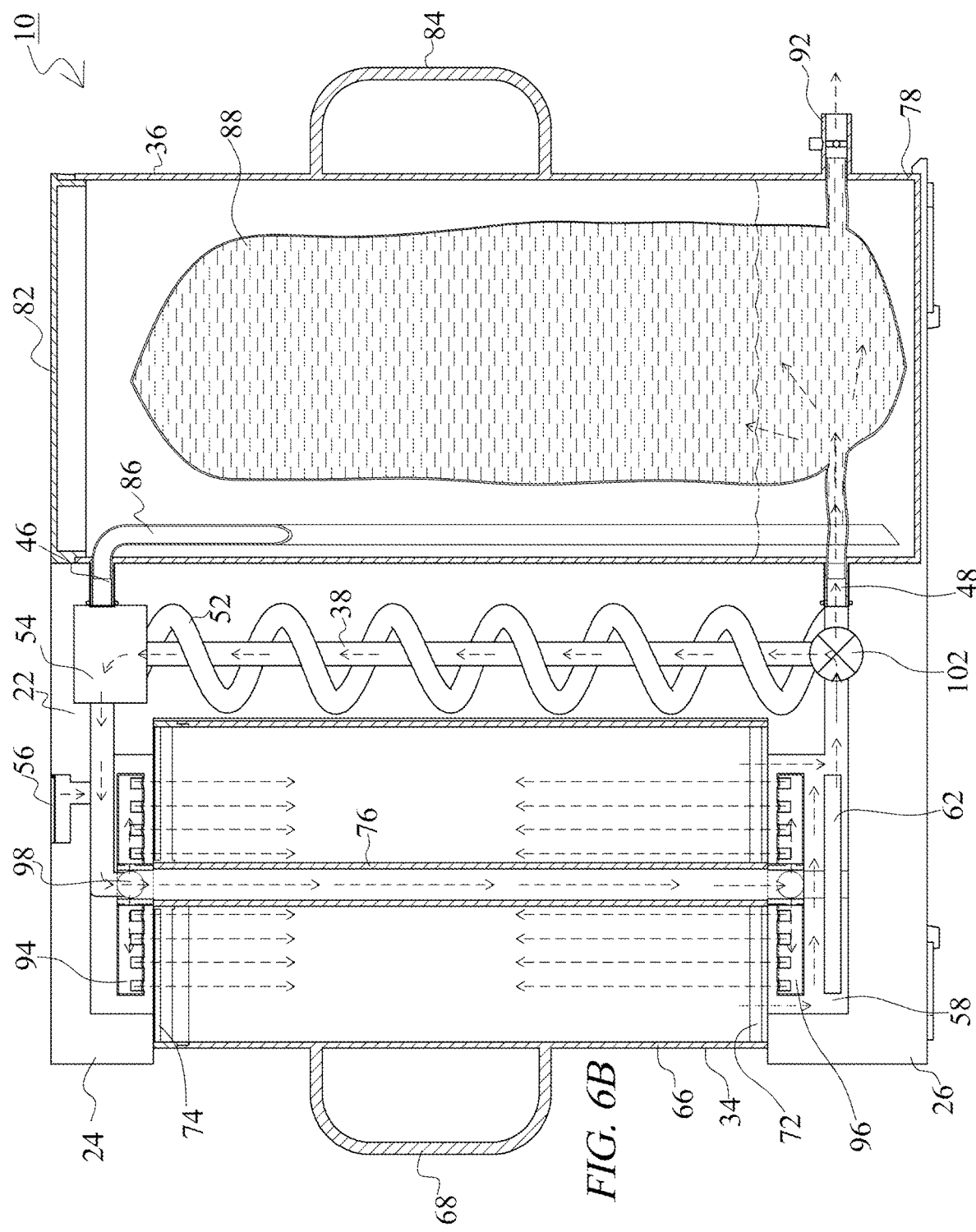
FIG. 6B is a sectional view showing the fluid recirculating into the collection bag of the reservoir.
Figure 8:
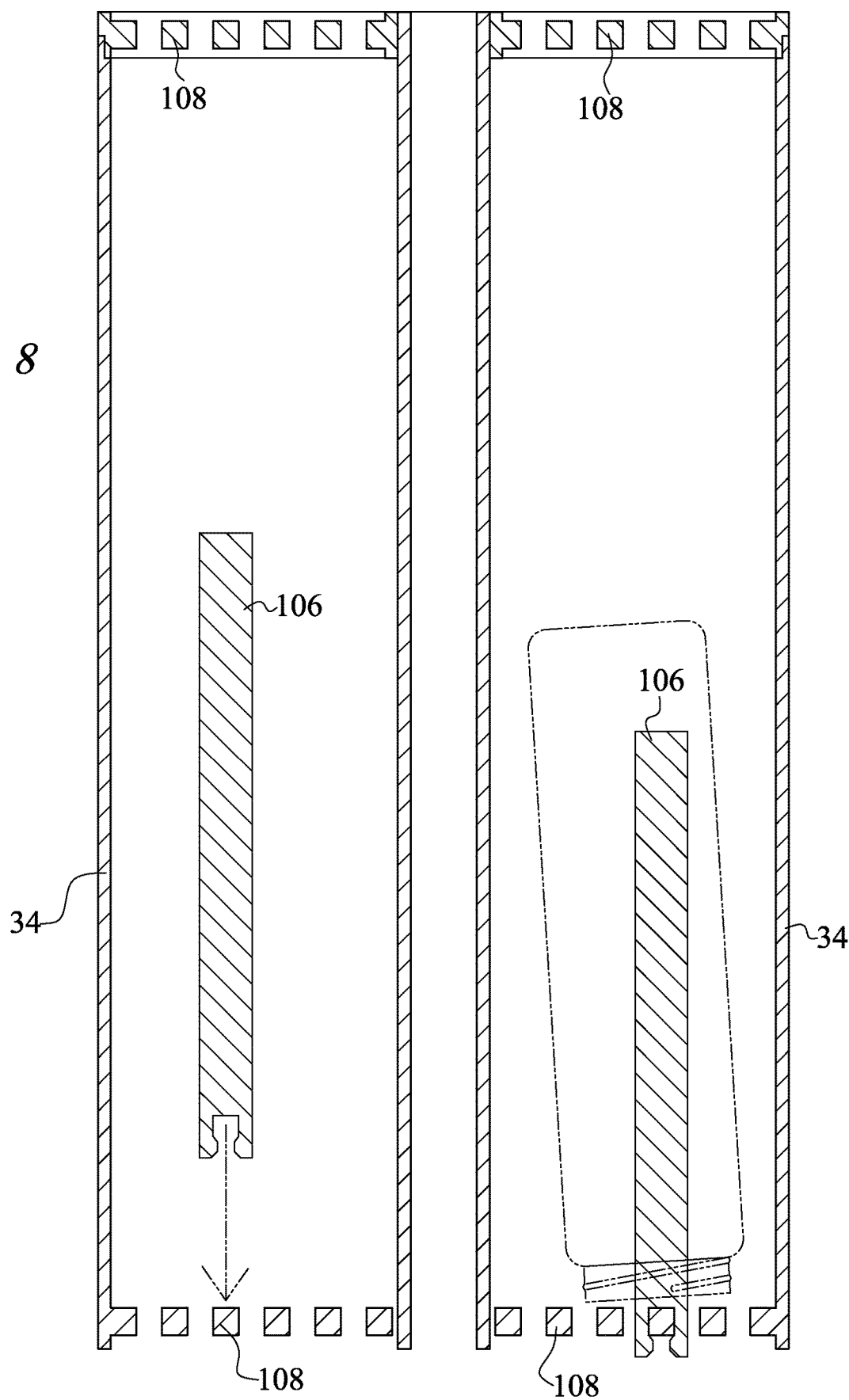
FIG. 8 is a sectional view of the container with detachable bottle stands.
Figure 9A:
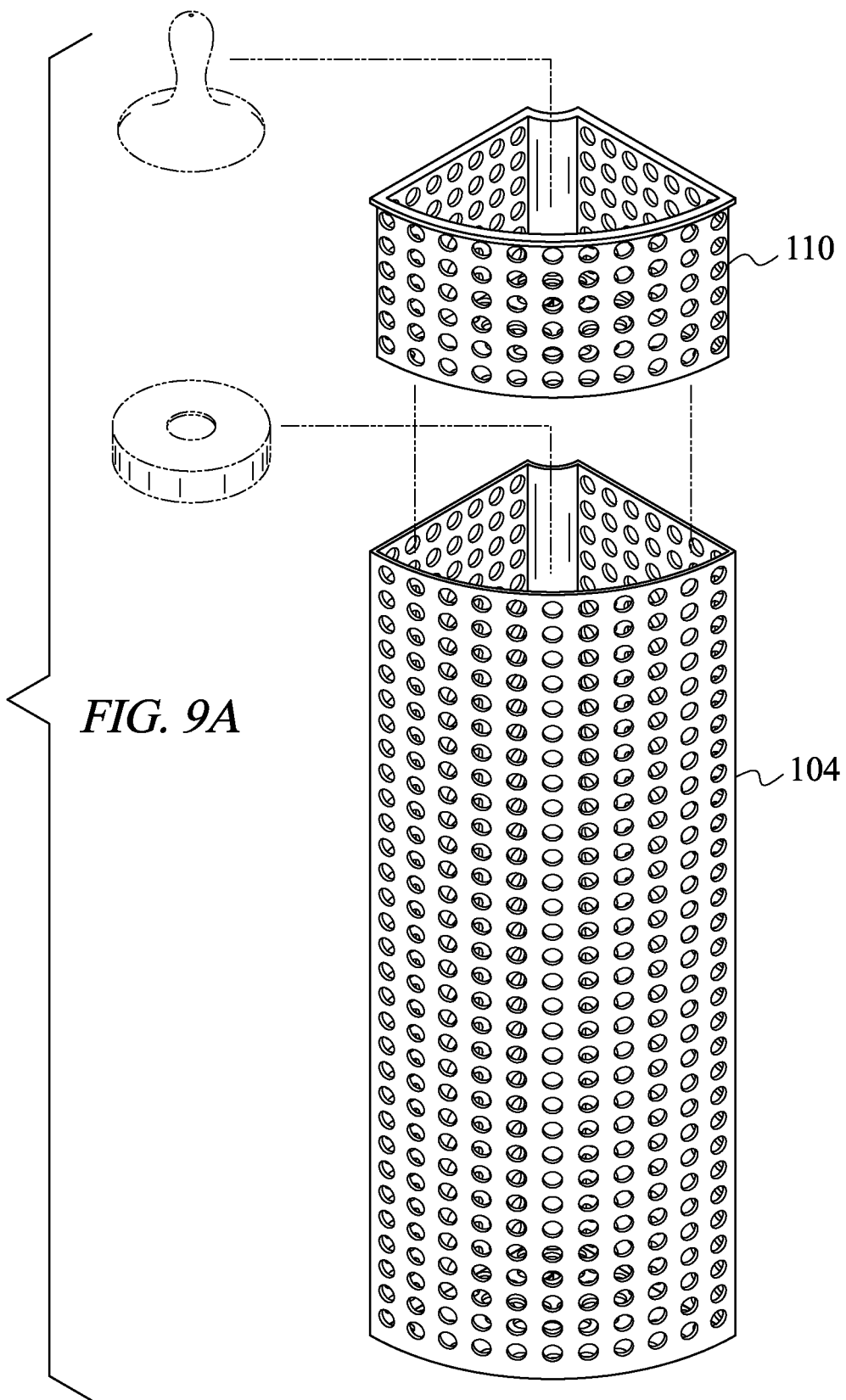
FIGS. 9A-B are perspective views of the basket and basket insert.
Figure 9B:
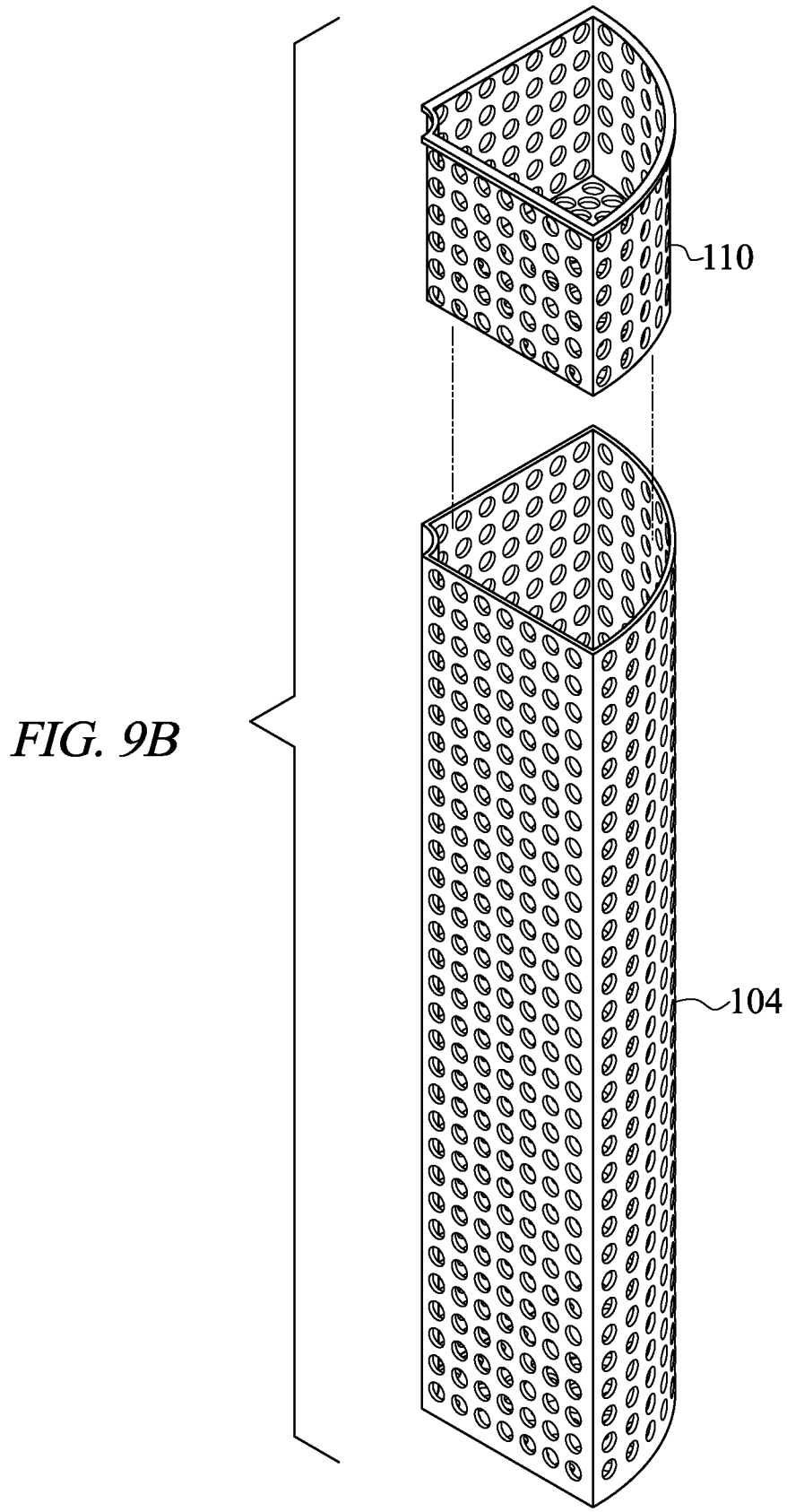
Figure 10:
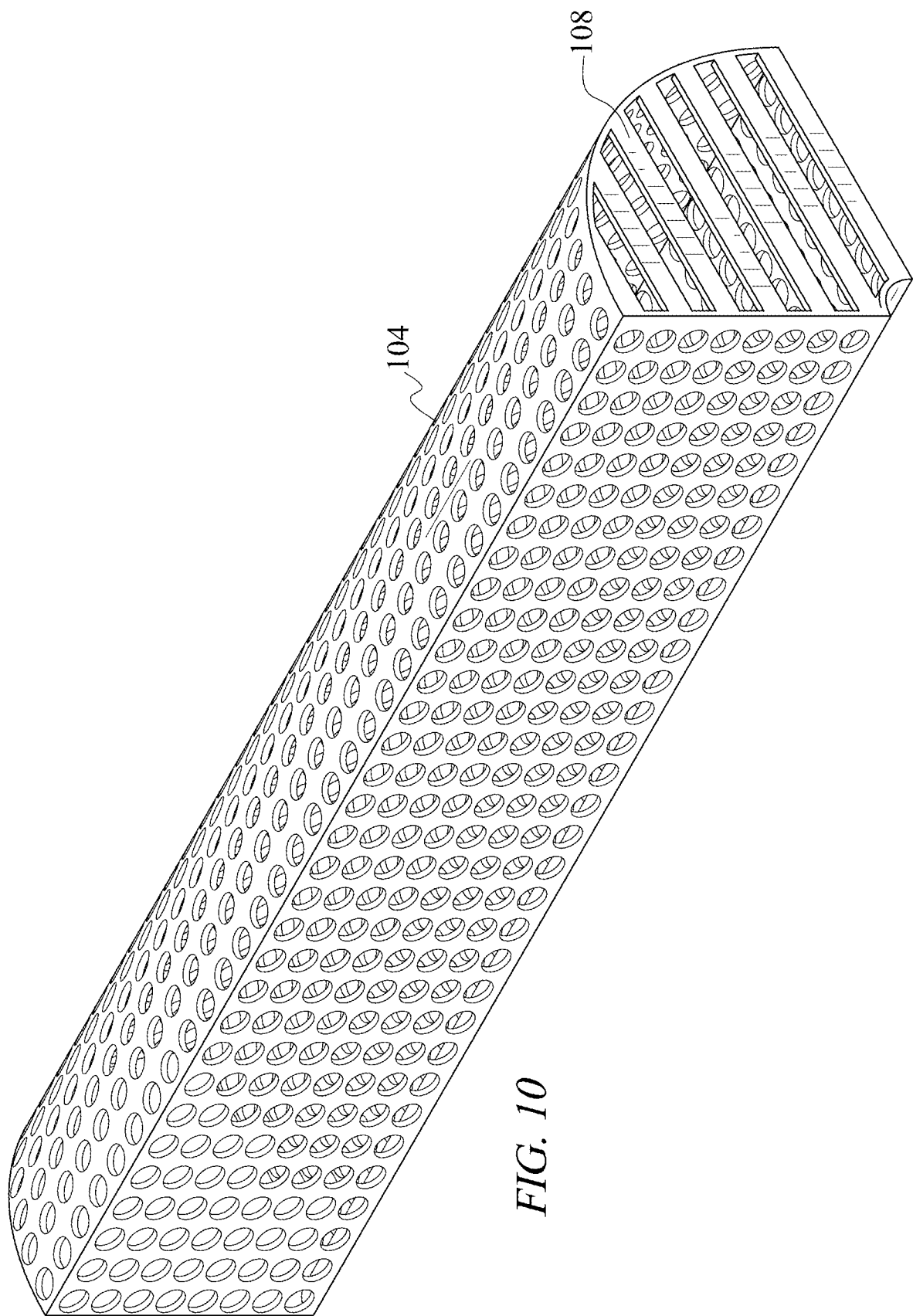
FIG. 10 is a perspective view of the basket insert.

The apparatus 10 is shown in FIG. 1 along with housing 22. Housing 22 is preferably defined by upper and lower portions (24 and 26) and first and second receiving areas (28 and 32) and is formed from a hardened impact resistant plastic. In the depicted embodiment, the receiving areas (28 and 32 of FIG. 3) are shaped to receive a cylindrical container 34 and reservoir 36. The exact geometry of the housing 22, however, does not form a part of the present invention. The entire apparatus 10 is preferably sized to enable it to be easily picked up and stored on a kitchen countertop. Resilient rubber feet may be secured to the underside of the housing to avoid marring. As elaborated upon hereinafter, housing 22 functions in routing water from reservoir 36 and into adjacent container 34 and back again. As such, housing 22 includes an internal water circulation line 38 (FIG. 6A).

First receiving area 28 of housing 22 includes both an upper and a lower portion that define an opening for container 34. First receiving area 28 further includes an upper water inlet 42 and a lower water outlet 44 for circulating water into and out of container 34 during a wash cycle. Second receiving area 32 likewise includes a water supply port 46 and a lower water return port 48 for routing water to and from the reservoir. The internal water recirculation line, 38 is in communication with inlet 42, outlet 44, return port 48, and supply port 46. A valve permits recirculation line 38 to by-pass reservoir 36 so that it may be continually reused during washing or rinsing cycles.

A coil shaped heating element 52 is positioned about water recirculation line 38 for use in heating the water during the wash and rinse cycle. Heating element 52 is preferably sufficient to raise the temperature of the water from ambient temperature to approximately 150° F. However, those of ordinary skill in the art will appreciate that the wash cycles described herein can be achieved at any number of desired temperatures.

A water pump 54 is also enclosed within housing 22 and is used in drawing water out of reservoir 36 and delivering it to container 34. Any number of pumps can be employed for this purpose. For example, the pump can be a conventional air pump. Nonetheless, displacement pumps and/or gear pumps may likewise be used. Pump 54 is preferably located in the upper portion 24 of housing 22 and draws a vacuum within recirculation line 38. Housing 22 further includes a detergent inlet 56 within its upper surface that allows a user to inject a cleaning element into the water recirculation line 38 during the wash cycle. A timed dispensing mechanism may optionally be included to dispense a preset amount of detergent at specified times during the wash cycle.

Water is evacuated from container 34 via a collection basin 58. More specifically, the lower portion 26 of first receiving area 28 includes a basin 58 for collecting the water as it drains from the lower surface of container 34. This water is then routed to lower water outlet 44 and either back to the recirculation line 38 or the return port 48 in a manner described below.

A heating element 62, such as a cylindrical hot plate heated by way of electrical resistance, is positioned within collection basin 58. Heating element 62 allows a small volume of the water to be converted into a hot steam to clean the articles during an initial phase of the washing cycle. Heating element 62, heating coil 52, and pump 54 can all be electrically powered via a conventional wall outlet and power cord 64.

Container 34 of apparatus 10 is described next. Container 34 is preferably cylindrical in shape with a transparent plastic sidewall 66. A handle 68 is included to facilitate carrying by a user. The bottom of the container is formed from a grate 72 to allow for the passage of water. An upper grate 74 is similarly included at the top of container 34. However, upper grate 74 is removable via a friction fit to allow items to be placed within container 34. A centrally disposed tube 76 runs between the opposing grates (72, 74) and creates a central fluid channel within container 34.

Container 34 is preferably large enough to store a wide variety of items that frequently need cleaning for an infant. These items include, but are not limited to, baby bottles, baby bottle liners, nipples, nipple rings, teething rings, sippy cups, valves, or any other item that are frequently used by a toddler or infant. The spacing of grates (72, 74) is preferably small enough to prevent passage of these items but large enough to allow for the passage of wash and rinse water. Container 34 is similarly dimensioned to be received between the upper and lower portions (24, 26) of first receiving area 28.

With container 34 properly positioned the upper end of tube 76 is placed in fluid communication with upper inlet 42. This allows water from inlet 42 to be delivered to the interior of container 34 in a manner described in greater detail. It also allows water from inlet 42 to be routed to central tube 76. The purpose of central tube 76 is described in greater detail hereinafter. The proper positioning of container 34 also places the lower grated surface 72 in fluid communication with both collection basin 58 and lower outlet 44. This ensures adequate evacuation of water from the interior of container 34.

Reservoir 36 is described next. Reservoir 36 resembles a conventional water pitcher and includes a closed lower surface 78 and a pivotal and/or removable upper lid 82. A handle 84 is likewise included. Again, reservoir 36 is preferably cylindrical in shape with plastic sidewalls, although other shapes and materials are within the scope of the present invention. Both a supply line 86 and a collection bag 88 are internally located within reservoir 36. With reservoir 36 properly positioned in the second receiving area 32, supply line 86 is coupled in a fluid tight manner to water supply port 46. Likewise, collection bag 88 is coupled in a fluid tight manner to return port 48. A water outlet spigot 92 is also formed through one of the side walls of reservoir 36 and is in communication with collection bag 88. The function of these various elements is described in greater detail hereinafter.

Water is preferably delivered to container 34 by way of upper and lower sprinklers (94, 96). More specifically, an upper sprinkler 94 is positioned within the upper portion 24 of first receiving area 28. This sprinkler includes several radial arms with associated apertures for the passage of water. Upper sprinkler 94 is in fluid communication with upper inlet 42. This allows water to be delivered to upper sprinkler 94 and into the radial arms. This, in turn, spins sprinkler 94 and delivers fluid downwardly into container 34 and over the associated contents.

A sprinkler valve 98 is also included for regulating the flow of water between upper sprinkler 94 and tube 76. Namely, sprinkler valve 98 has a first position where fluid is delivered exclusively to upper sprinkler 94 and fluid is prevented from entering the central tube 76. In the second position, fluid is delivered to both upper sprinkler 94 and tube 76. In this second orientation, fluid is delivered over the contents of the container by both the upper and the lower sprinklers (94, 96). Namely, water from central tube 76 is delivered to lower sprinkler 96.

This lower sprinkler 96 is positioned within the lower portion 26 of first receiving area 28 and is in communication with tube 76. Thus, when the sprinkler valve 98 is in the second position water is delivered to tube 76 and into lower sprinkler 96. The lower sprinkler 96 has a similar construction to that of the upper sprinkler 94. Water delivered to lower sprinkler 96 shoots water upwardly into container 34. Thus, with the sprinkler valve 98 in the second position, both the upper and the lower sprinklers (94, 96) are activated to more effectively cleanse the contents of container 34.

In an alternative embodiment, an additional valve 99 is positioned within the lower sprinkler 96. Valve 99 is similar in construction to valve 98. Valve 99, however, regulates the flow of water between the arms of lower sprinkler 96 and heating element 62. More specifically, in a first position of valve 99, water from central tube 76 is routed to the arms of lower sprinkler 96 and distributed to the interior of container 34. In a second position of valve 99, water is instead routed downwardly through the sprinkler 96 and onto heating element 62. Thus, valve 99 can be used to supply a small volume of water, approximately 3-4 oz, to the heating element so that steam can be generated in an initial phase of cleaning. This initial phase would loosen debris and food and otherwise prepare the contents of container 34 for cleaning.

Housing 22 also includes an exit valve 102. Exit valve 102 has a first position wherein fluid from the lower outlet 44 is delivered back to recirculation line 38. In this orientation water that collects in collection basin 58 is delivered to the outlet 44 and then back upwardly through recirculation line 38 by way of pump 54. As the water is being recirculated it is also heated by the coil shaped heating element 52. This has the effect of heating the water to a degree suitable for cleaning. This recirculated water may also encounter detergent adjacent the detergent inlet 56. This heated and detergent filled water is then passed again through container 34 by way of the upper and lower sprinklers (94, 96). This water can be continually recirculated for a predetermined number of cycles.

Thereafter, exit valve 102 is brought into its second position. In the second position, water from the lower outlet 44 is delivered to return port 48 and to collection bag 88. Namely, once the desired degree of washing is completed, water is evacuated and delivered to collection bag 88. In this manner, dirty water does not come in contact with the interior of reservoir 36 but is segregated by way of collection bag 88. Once all the water is evacuated it may be dispensed of by opening water spigot 92 and applying pressure upon collection bag 88. In the alternative, bag 88 can be replaced by a length of retractable tubing that routes the used water to a drain.

The operation of the apparatus is described next. The user would begin the process by first removing reservoir 36 and opening lid 82. Reservoir 36 is then filled with water. Lid 82 is replaced and reservoir 36 is secured within second receiving area 32. At this point, the user should ensure that the water supply line 86 and the collection bag 88 are tightly secured to the associated ports (46, 48).

Next, container 34 is removed and the top grate uncoupled 74. Items to be cleaned are then placed within container 34 and top grate 74 is repositioned. Container 34 is then placed within the first receiving area 28. When properly positioned tube 76 is in communication with water inlet 42 and lower grate 72 of container 34 is positioned over collection basin 58. Apparatus 10 is then plugged in and turned on and heating coil 52 and heating plate 62 begin to heat.

Although there are many types of washing cycles that can be carried out with this invention, a preferred mode is as follows. A small amount of water is pulled from reservoir 36 by way of pump 54 (which draws a vacuum on supply line 86). The sprinkler and exit valves (98, 102) are placed in the first position. This small amount of water is circulated by way of upper sprinkler 94 and showers fluid down onto the hot plate. In the alternative, the small amount of water can be delivered through lower sprinkler 96 via valve 99 as described above and also as the water drains downwardly within collection basin 58, it contacts the heating plate 62 and becomes vaporized. Both options result in a heated water vapor being applied to all the contents of container 34, which loosens any debris and prepares the contents for the wash cycle.

Once this cycle is complete, the sprinkler valve 98 is placed in the second position and more water is drawn from reservoir 36 (again via pump 54) in a cleaning phase. The water used in this phase represents approximately ⅓ of the total volume of reservoir 36. In this phase water is delivered to the interior of container 34 by way of both the upper and lower sprinklers (94, 96) as a result of the sprinkler valve 98 being in the second position or sprinkler valve 99 being in the first position. The recirculated water is heated by way of cylindrical heating coil 52 and detergent is added by way of detergent inlet 56. This water continually cycles for a predetermined number of times in order to accomplish a thorough degree of cleaning. For instance, the water may cycle through ten or more times to ensure sufficient cleaning. Thereafter the exit valve 102 is opened and the cleaning water is evacuated to collection bag 88 or dispersed through a retractable tube into an outside drain. Thereafter a rinsing phase would be commenced. A timer, which may be embodied in a microprocessor or microcontroller, can be included for timing the length of the various cycles and operating valves (98, 102) at appropriate intervals.

In the rinsing phase exit valve 102 is positioned back to the first position and the remaining water is delivered to container 34 both by way of the upper and lower sprinklers (94, 96). However, in this mode no detergent is used. The rinsing phase ensures that all the detergent and/or residue is removed from the baby items. This cycle continues for a predetermined number of cycles. Once complete, exit valve 102 is rotated to the second position and the water is evacuated to collection bag 88 or retractable tube.

Finally, after the final wash cycle heating coils 52 are turned off, heating plate 62 remains on to continue the heating and drying of the contents of container 34. If desired, the lower sprinkler 96 could be powered by way of a small motor to act as a fan to ensure the proper circulation of the heated air. Additionally, heating plate 62 can optionally generate heat throughout all cleaning phases to assist with sterilization and drying.

Container 34 can also be used in conjunction with one or more baskets 104. The depicted baskets 104 are pie shaped and have a length that is substantially the same as container 34. Basket 104 can include a removable lid and is adapted to be inserted into a portion of container 34. Basket 104 functions in retaining smaller infant items such as caps or other bottle accessories during washing. Baskets 104 are preferably shaped such that one or more baskets can be used while still leaving a portion of container 34 free for other larger items, such as bottles. A smaller subbasket insert 110 can also be used in conjunction with basket 104 to house delicate items such as nipples or binkies. Insert 110 can rest within the upper opening of the larger basket 104.

Additionally, one or more posts 106 can be used to support bottles within container 34. Posts 106 include a female lower portion that is dimensioned to be snap fit onto individual grates 108 within the lower portion 72 of container 34. Posts 106 function in retaining bottles upright during the wash cycle.

Alternative Embodiment

An alternative embodiment of the portable washing apparatus is illustrated in FIGS. 11 through 14. Although the construction and configuration of this alternative apparatus 200 is different from the embodiment disclosed above, its function and operation are similar. Namely, apparatus 200 includes a housing 202 into which various articles to be washed are placed for cleaning. As with the primary embodiment, apparatus 200 is both portable and self-contained and does not need to be coupled to an external water supply. As such, apparatus 200 lends itself to washing infant related articles such as bottles, nipples, toys, and/or teething rings.

Housing 202, as with the majority of the internal components, is preferably formed from a heavy duty impact resist plastic material. A control panel 204 is formed within one side of the housing 202 and permits the user to monitor the various cycles of the washing operations.

Figure 11:
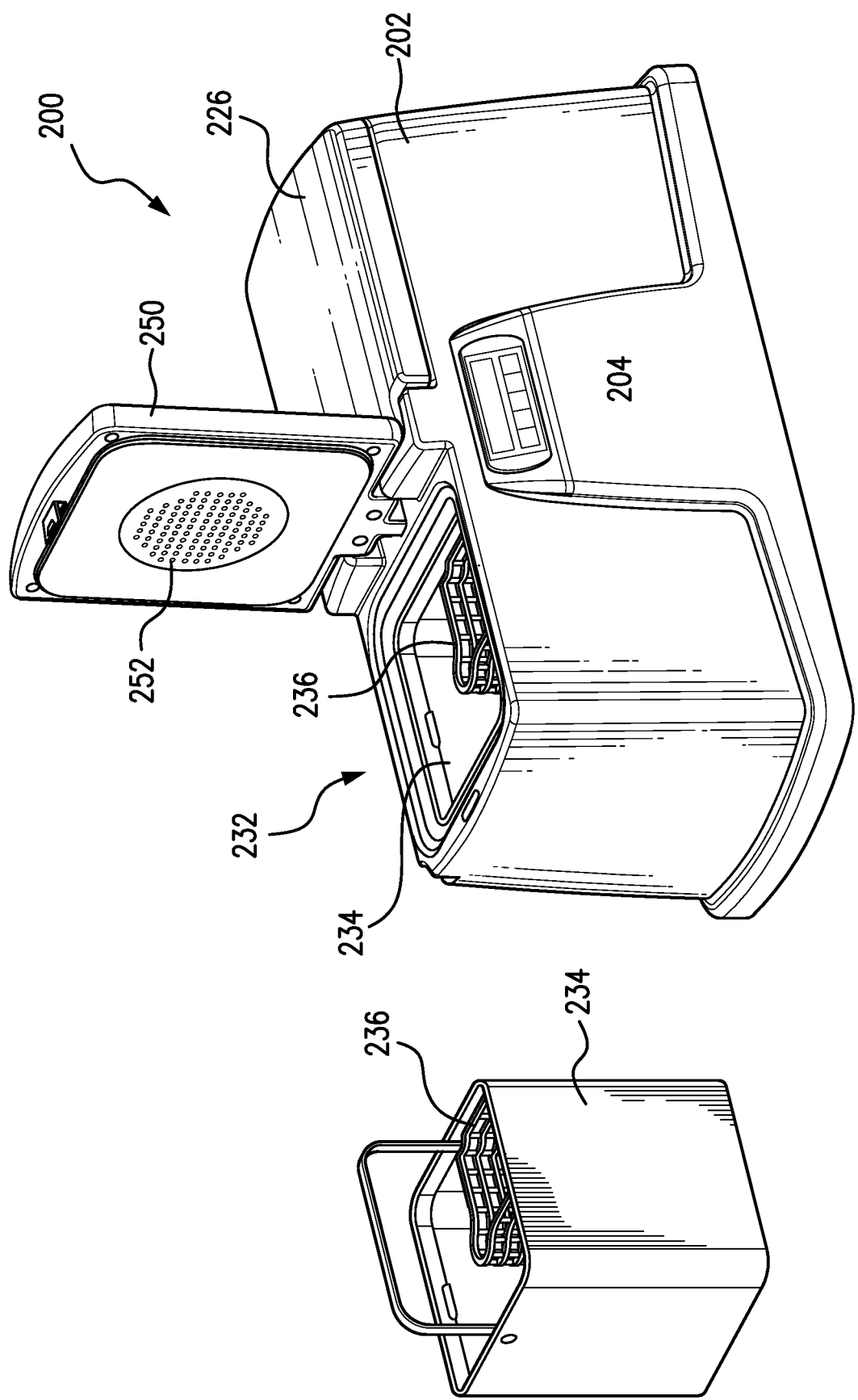
FIG. 11 is a perspective view of an alternative embodiment of the washing apparatus.
Figure 12:
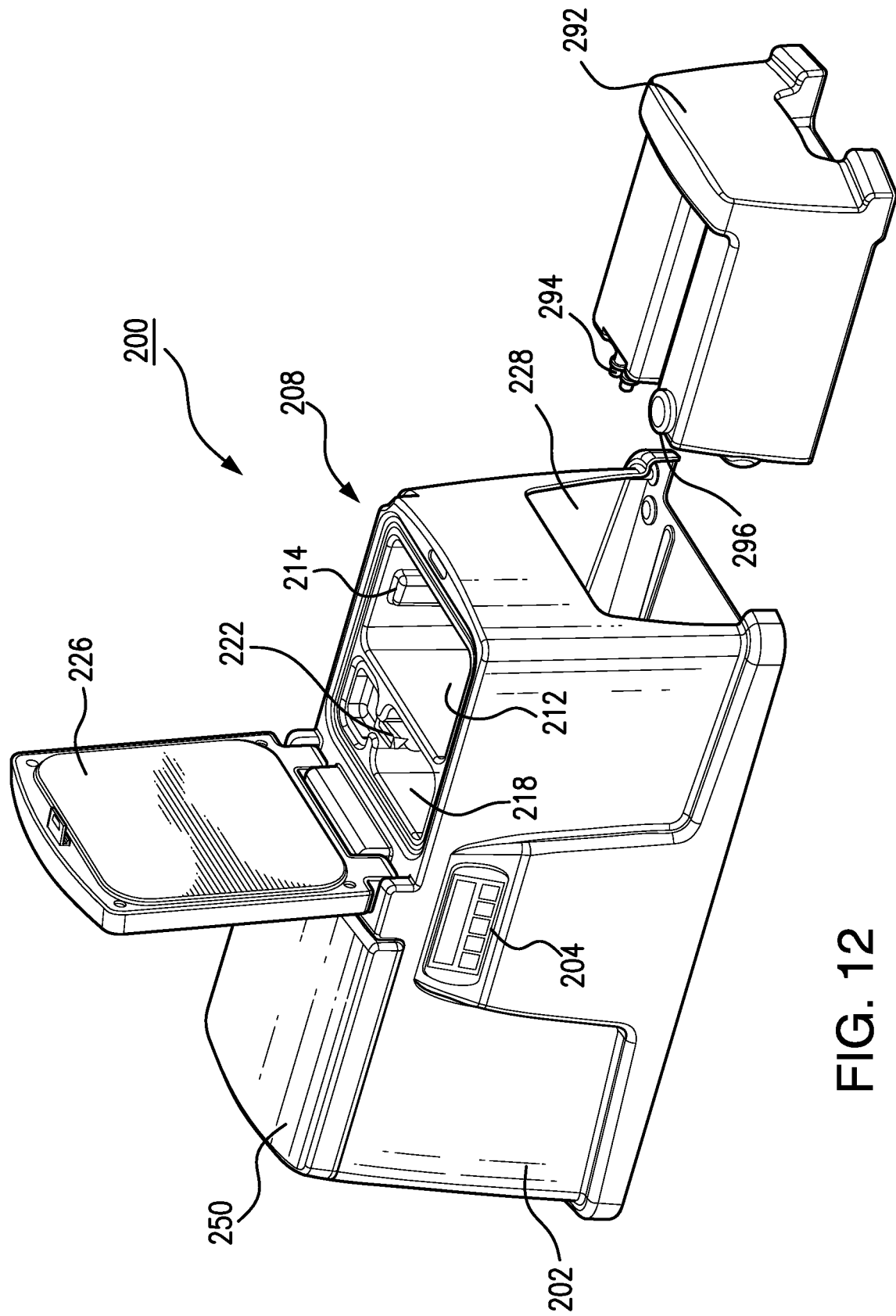
FIG. 12 is an additional perspective view of the alternative embodiment of FIG. 11.
Figure 13B:
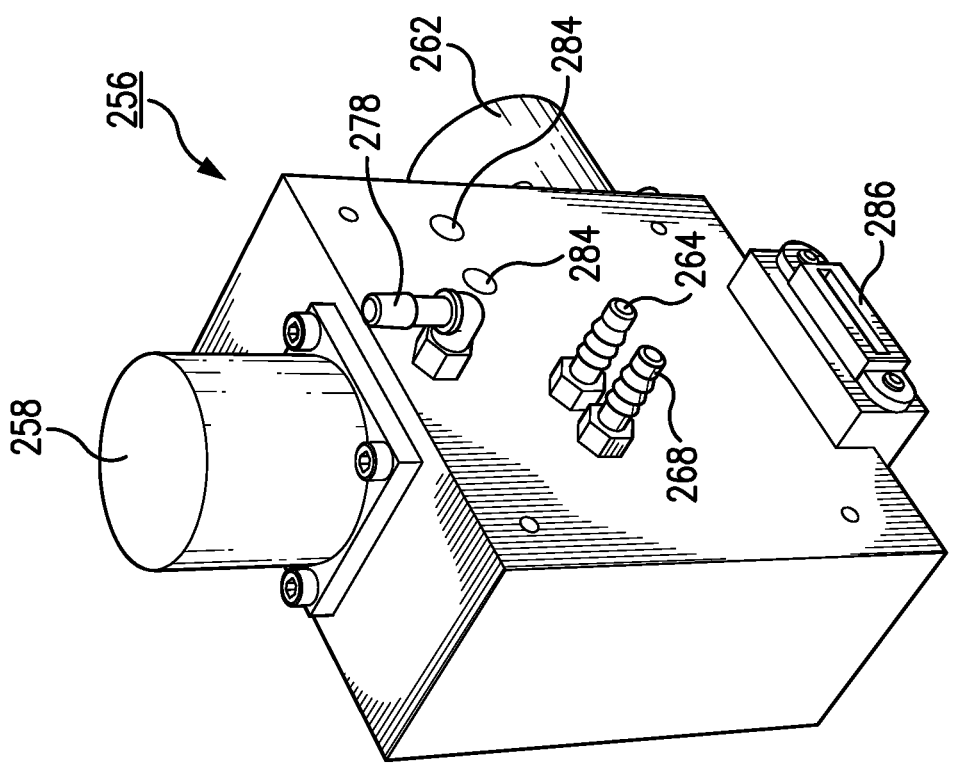
FIGS. 13A and 13B are perspective views of the manifold employed by the alternative embodiment of FIG. 11.
Figure 13A:
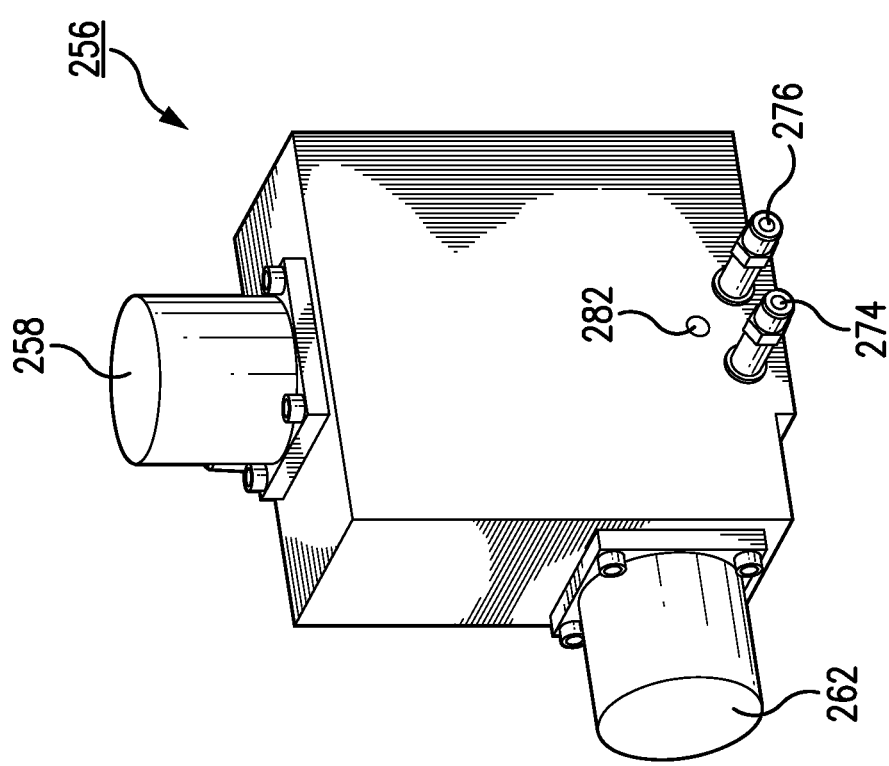
Figure 14:
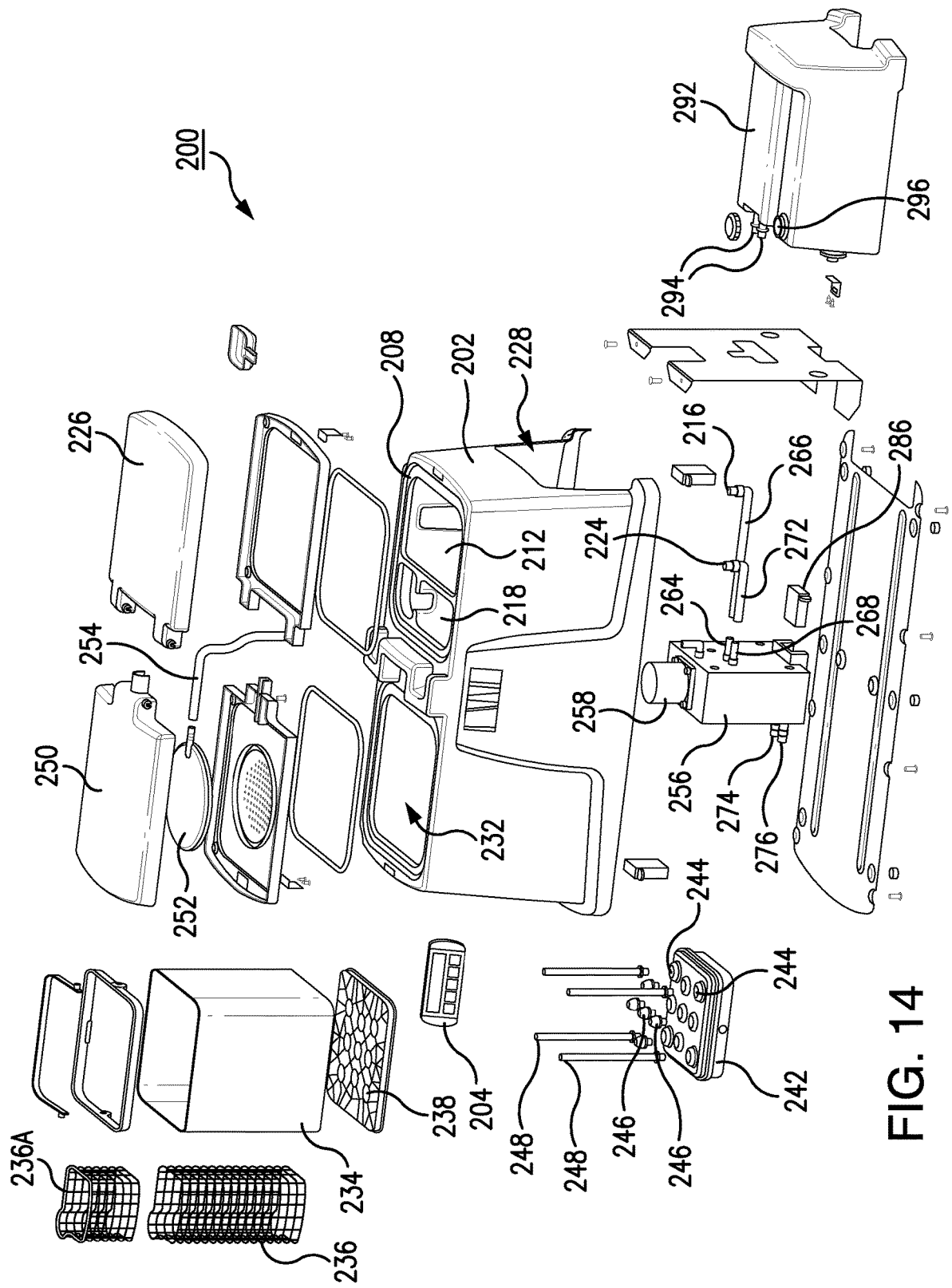
FIG. 14 is an exploded view of the alternative embodiment of FIG. 11.
Figure 15:
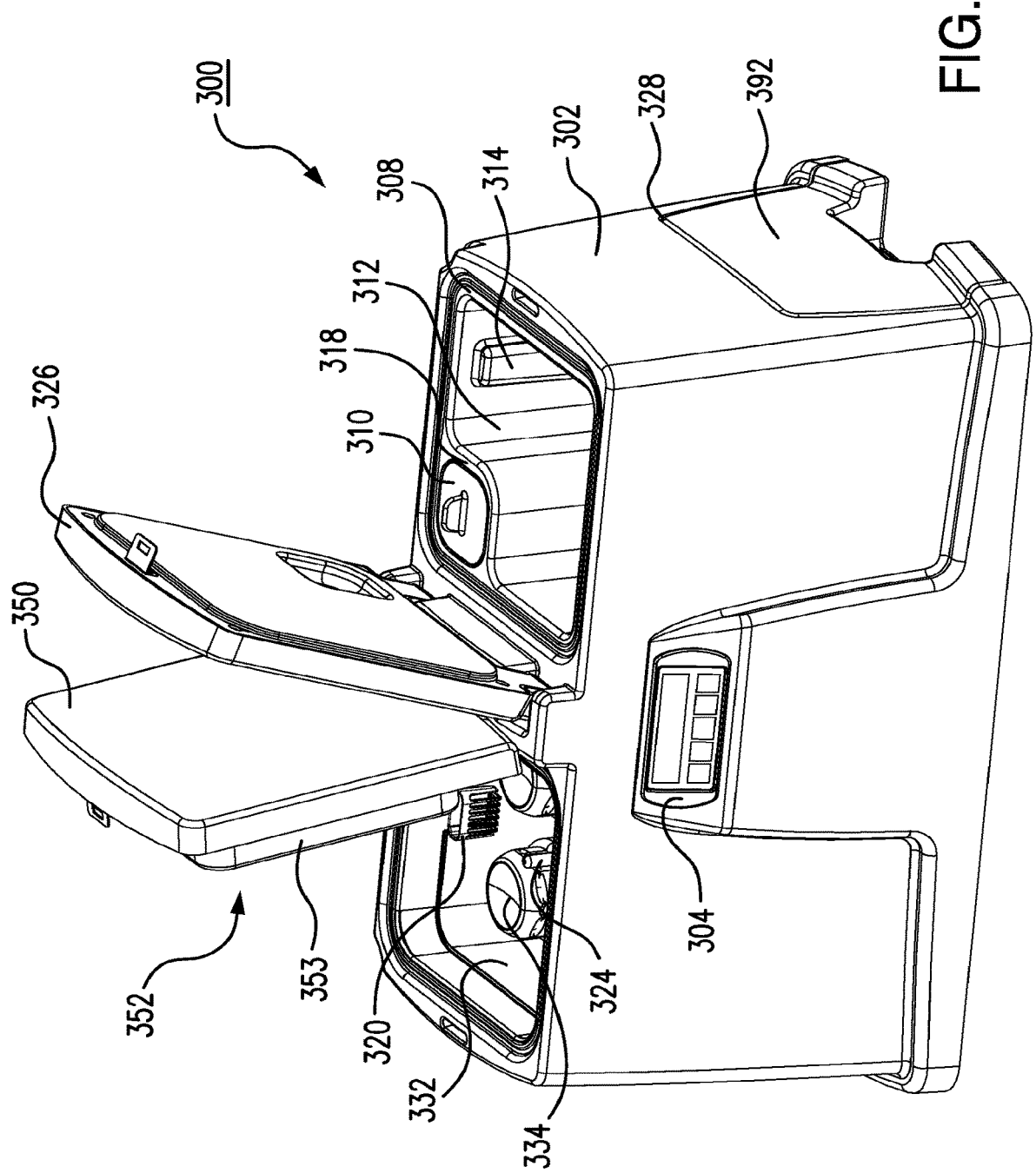
FIG. 15 is a perspective view of a second alternative embodiment of the washing apparatus.
Figure 16:
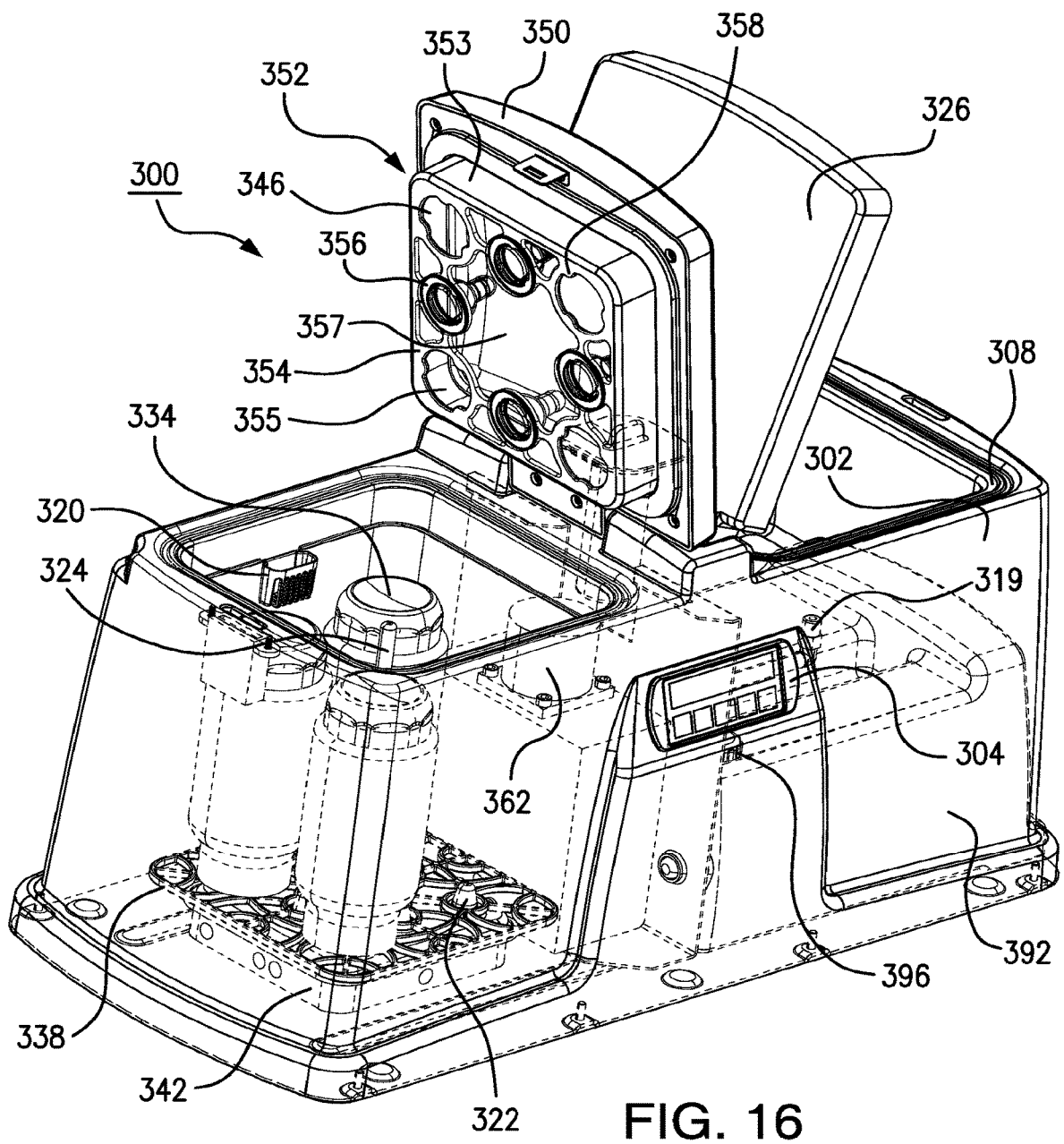
FIG. 16 is an additional perspective view of the second alternative embodiment of the washing apparatus.
Figure 17:
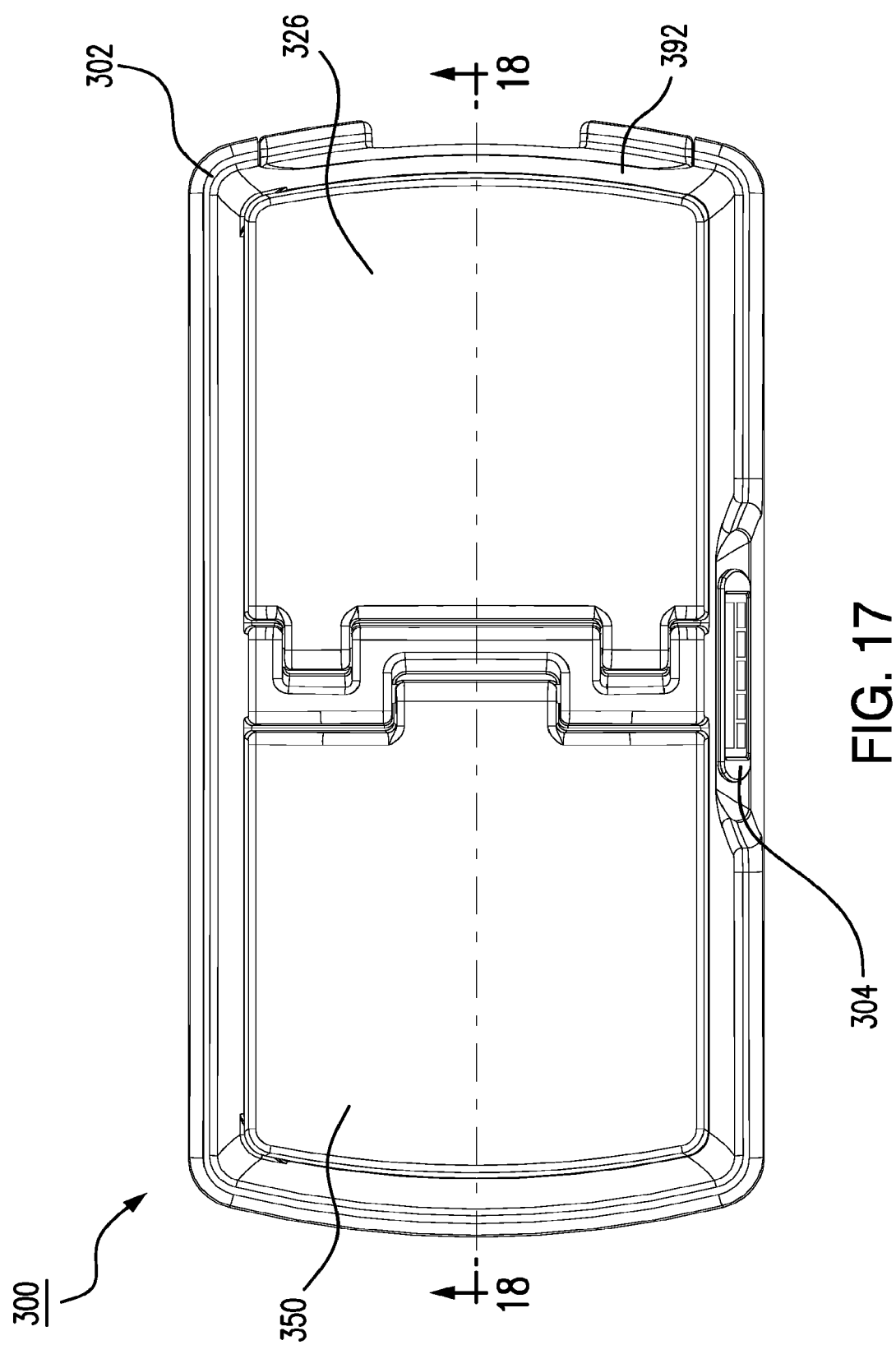
FIG. 17 is a top plan view of the second alternative embodiment of the washing apparatus.
Figure 18:
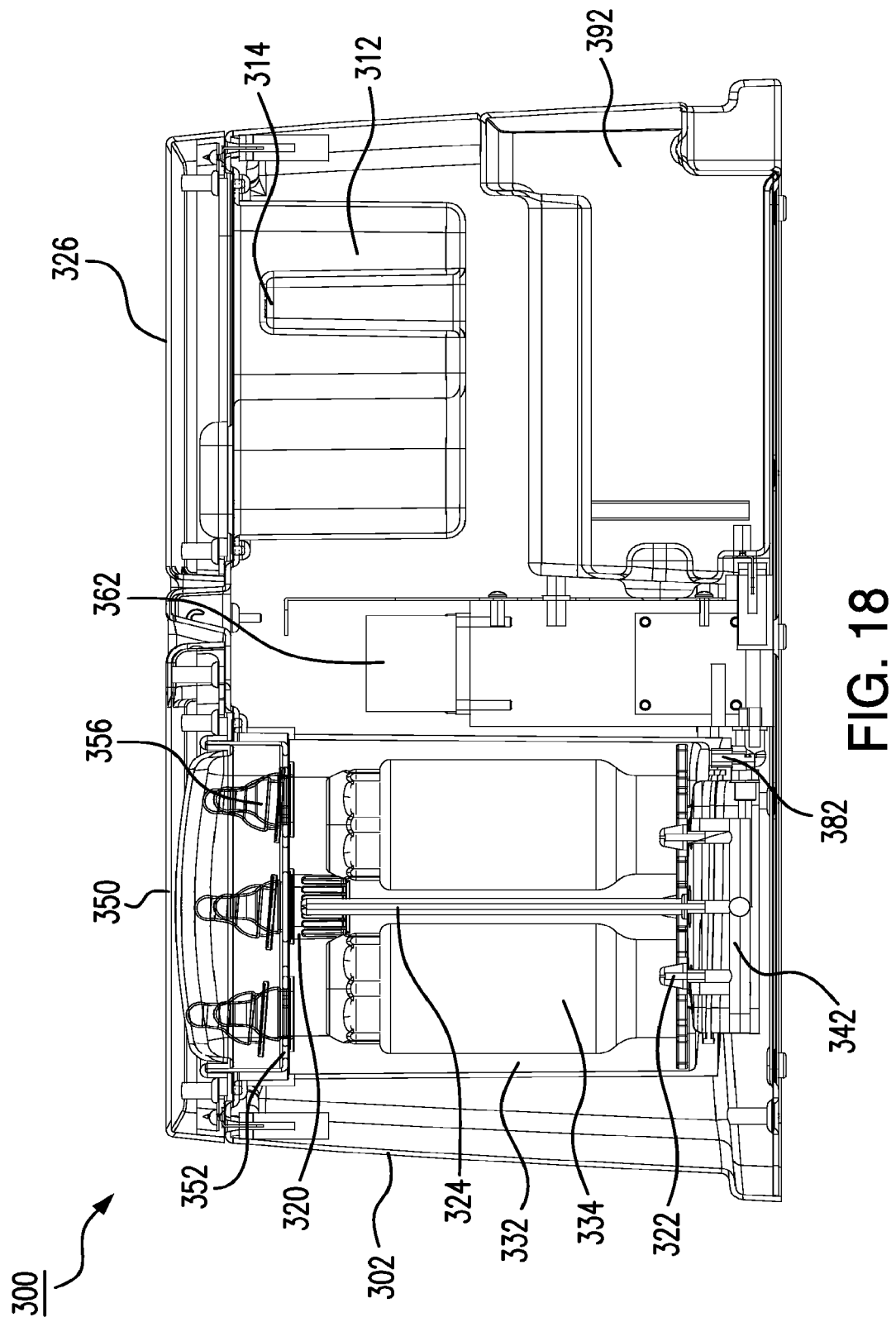
FIG. 18 is a side view of the second alternative embodiment of the washing apparatus.

As noted in FIGS. 11-12, housing 202, in the preferred embodiment, is equally divided into two halves. The first half constitutes a fluid chamber 208 and the other half constitutes a washing chamber 232. Fluid chamber 208, in turn, is divided into a rinse water container 212 and a water detergent container 218. Water containers 212 and 218 are reservoirs that are each adapted to receive a volume of water supplied by the user. In the preferred embodiment, apparatus 200 can complete full wash and rinse cycles with six cups of water. Detergent water container 218 contains a recess that houses a scoop used to measure the amount of cleaning detergent needed for the wash cycle. The detergent can be any of a number of commonly available dishwasher detergents. During the machine preparation the user fills container 218 with clean water to the level indicator 222, then pours detergent in with the scoop provided. The user can then use the scoop to mix the detergent and water within container 218. Thereafter, the scoop can be placed back in the holder. A detergent outlet port 224 is formed at the bottom of container 218 for use in allowing the detergent filled water to be directed to the manifold 256.

A level indicator 214 is also positioned within the container 212 and is for use in determining when the proper volume of rinse water is achieved. A water outlet port 216 is formed in the bottom of a water container 212 and allows the water to be directed to the manifold 256.

Both the rinse water and water-detergent container (212 and 218) are covered by a pivotal lid. Namely, lid 226 is secured over the fluid chamber 208 and a lid 250 is secured over washing chamber 232. These lids can be selectively locked by solenoids during the wash cycle to prevent user access. A water tight seal is achieved between lids 226 and 250 and housing 202 via a series of gaskets. The fluid chamber 208 side of housing 202 includes an opening 228 at its base to allow insertion of a waste water container, as described in more detail hereinafter.

Washing chamber 232 is a large opening into which both a bottle container 234 and an insert basket 236 can be positioned. Bottle container 234 and insert basket 236 allow articles to be stored for cleaning. For example, smaller, loose articles such as nipples and teething rings may be placed in basket 236. A smaller sub-basket 236A may also be positioned within basket 236 to house nipples or binkies. Larger items such as bottles may then be placed within container 234 and outside of basket 236. A grid 238 is formed at the bottom of the bottle basket 234 and permits the free flow of fluid through the bottom of container 234. Bottle container 234 is placed in registry with the grid 238 and a hot plate 242. Hot plate 242 is for use in directing water upwardly into the bottle container 234 during washing operations.

Water is introduced upwardly into container 234 by a series openings in the hot plate base 242. In the preferred and depicted embodiment there are a series of nine openings. In the preferred embodiment, bottle washer would come supplied with the following unattached accessories: four tree-type sprayers 248; nine jet-bullet sprayers 246; and eight blanks 244. However, the use of different accessories and in other configurations is within the scope of the present invention. These unattached devices need to be screwed into the openings by the user who, as depicted, may attach them in the configuration shown in FIG. 14. Both sprayers 246 and 248 serve the same function of routing water upwardly through grid 238 into the bottle container 234. However, jet sprayers 246 have a lower profile than tree sprayers 248. In this regard the tree sprayers 248 are particularly adapted to be inserted into an infant bottle to insure that the entire internal volume is cleaned. The blanks 244 are provided to stop the flow of water through the designated openings allowing the user flexibility in how they want water directed upward. For example blanks 244 could be placed in the openings on the outside of the base and a bullet sprayer 246 placed in the center to direct water into the center of the wash chamber 232. Washing chamber 232 further includes a shower sprayer 252 at its upper most extent. The shower sprayer 252 is mounted within a lid 250 whereby water is directed in a direction opposite to the water coming from the water jet bullet sprayers 244 and tree sprayers 248. Shower sprayer 252 therefore cleans the external surfaces of the articles. A length of flexible hosing 254 is used to direct water upwardly into the shower sprayer 252.

Apparatus 200 further includes a manifold 256. A cam motor 258 and a pump 262 are mounted upon manifold 256. Cam motor 258 operates a cam that, in turn, cycles a series of flapper valves between opened and closed orientations. Prior to apparatus 200 being turned on, manifold 256 initially keeps rinse water and detergent water outlet ports 216 and 224 closed. Pump 262 is motorized via an electric motor. Pump 262 functions in driving water into the manifold 256 via inlet ports 268 and 264 and outlet ports 274, 276 and 278, or into waste water outlet ports 284. A heater is included within manifold 256 for heating water being pushed through the manifold 256.

Manifold 256 includes a rinse water inlet port 264 that is connected to the water outlet port 216 of fluid of water container 212 by way of a line 266. Likewise manifold 256 includes a detergent water inlet port 268 which is connected to the detergent outlet port 224 by way of a detergent line 272. Once apparatus 200 is turned on, cam motor 256 opens water and detergent outlet ports 216 and 224 in a predesigned sequence. As a result, water and detergent are delivered from the fluid chamber 208 and into the interior of manifold 256 for heating.

A jet sprayer outlet port 274 and a tree sprayer outlet port 276 thereafter route heated fluid from the manifold 256 into the jet sprayers 246 and tree sprayers 248 respectively. Similarly a shower sprayer outlet port 278 routes cleaning or rinsing fluid from the manifold 256 to the shower sprayer 252. This fluid is routed by way of intake line 254. Once the detergent or rinse water is delivered from the sprayers (246, 248) and shower 252 it is collected within the hot plate 242. Hot plate 242 is tiled and routes the water to a recirculation inlet port 282 within manifold. Pump 262 operates to take this recirculated water and deliver it back out to jet sprayers 246, tree sprayers 248 and shower sprayers 252. The detergent or rinse water is re-circulated multiple times in this fashion until it reaches an optimal temperature of 150 degrees Fahrenheit. The number of cycles needed to attain this optimal temperature can vary. Also, it is within the scope of the present invention to change the number of required cycles or the optimal temperature of the detergent or rinse water. A temperature sensor, timer, and microprocessor are included for regulating the length of the wash cycle.

Once the number of cycles is complete, cam motor 258 operates again to close the jet outlet port 274, tree sprayer outlet port 276, and shower sprayer outlet port 278. Moreover the cam motor 258 opens a series of waste water outlet ports 284. This permits the waste water to be delivered out of the manifold 256 and into a waste water container 292. A vent located on the back side of the machine in the midsection is attached to tubing that is connected to the manifold 256. During the final cycle instead of the pump sucking up recirculating water through inlet port 282, the pump sucks up steam and hot air and pushes it out through the tubing (not depicted) and vent (not depicted) drying and cooling the contents.

Waste water container 292 is adapted to fit within the opening 228 of housing 202. The waste water is collected into the water container 292 through a series of waste water inlet ports 294 that are coupled to outlet ports 284. Thereafter once wash and rinse cycle operations are complete the waste water container 292 can be removed from housing 202 and the water drained by way of port 296. Additionally waste water container 292 includes a male latch 298 that is adapted to cooperate with a female latch 286 upon manifold this can insure that the system 200 cannot operate without the waste water container properly coupled. In the preferred embodiment, latches 298 and 286 can be locked together via a solenoid.

Second Alternative Embodiment

Another alternative embodiment of the portable washing apparatus is illustrated in FIGS. 15 through 19. Although the construction and configuration of this alternative apparatus is different from the embodiments disclosed above, its function and operation are similar. Namely, apparatus 300 includes a housing 302 into which various articles to be washed are placed for cleaning. As with the other embodiments, apparatus 300 is both portable and self-contained and does not need to be coupled to an external water supply. As such, apparatus 300 lends itself to washing infant related articles such as bottles, nipples, toys, and/or teething rings.

Housing 302, as with the majority of the internal components, is preferably formed from a heavy duty impact resist plastic material. A control panel 304 is integrally formed within one side of the housing 302 and permits the user to monitor the various cycles of the washing operations.

As noted in FIGS. 15-19, housing 302, in a preferred embodiment, is equally divided into two halves. The first half constitutes a fluid chamber 308 and the other half constitutes a washing chamber 332. Fluid chamber 308, in turn, is divided into a rinse water container 312 and a filter container 318. Rinse water container 312 is adapted to receive a volume of water supplied by the user. Filter container 318 is adapted to receive a water filter 310 for filtering water prior to entry into the pump. In one embodiment of the invention, the filter is a 50 micron filter. In the preferred embodiment, apparatus 300 can complete full wash and rinse cycles with six cups of water, the cycles including a pre-rinse cycle, a detergent cycle, a first rinse cycle, and a second rinse cycle. Washing chamber 332 contains a lower supply port 317 for receiving water from the fluid chamber 308 and a detergent basket 320 integrally formed within an interior wall of the washing chamber 332 for accommodating a detergent. The detergent can be any of a number of commonly available dishwasher detergents. During the machine preparation the user fills rinse water container 312 with clean water to a level indicator 314, then pours detergent in the detergent basket 320 with a scoop provided. Thereafter, the scoop can be placed back in the provided holder. Level indicator 314 is positioned within the rinse water container 312 and is for use in determining when the proper volume of rinse water is achieved. A water outlet port 316 is formed in the bottom of the rinse water container 312 and allows the water to be directed to the washing chamber 332.

Apparatus 300 further comprises an internal water line 319 positioned within the housing 302 and interconnecting the lower outlet port 316 and the lower supply port 317, the internal water line 319 in communication with a first solenoid valve 368 that controls the flow of rinse water from the rinse water container 312 to the washing chamber 332.

Both the rinse water and filter container (312 and 318) are covered by a pivotal lid. Namely, lid 326 is secured over the fluid chamber 308 and a lid 350 is secured over washing chamber 332. In one embodiment of the invention, the interior of lid 350 is convex, or domed. These lids can be selectively locked by solenoids or latch circuit during the wash cycle to prevent user access. A water tight seal is achieved between lids 326 and 350 and housing 302 via a series of gaskets. The fluid chamber 308 side of housing 302 includes an opening 328 at its base to allow insertion of a waste water container 392, as described in more detail hereinafter.

Washing chamber 332 is a large opening into which both bottles 334 and an insert basket can be positioned. Insert basket allows articles to be stored for cleaning. For example, smaller, loose articles such as nipples and teething rings may be placed in basket. A smaller sub-basket may also be positioned within insert basket to house nipples or binkies. Larger items such as bottles may then be placed within washing chamber 332 and outside of basket. A grid 338 is formed at the bottom of the washing chamber 332 and permits the free flow of fluid into the washing chamber 332 and through the bottom of insert basket. Within the washing chamber 332 is a jet sprayer manifold 342 in fluid communication with both a plurality of jet sprayers 322 and a center jet sprayer 324, the plurality of jet sprayers 322 and the center jet sprayer 324 each comprising a proximal end and a distal end, wherein the proximal end is connected to the jet sprayer manifold 342 and the distal end comprises an opening for spraying rinse water therethrough and configured for directing water upwardly during washing operations, and wherein the distal end of the center jet sprayer 324 is proximate an accessory holder 352 (described below) for directing rinse water therethrough. Bottles 334 and insert basket are placed in registry with a series of jet sprayers 322. The plurality of jet sprayers 322 and the center jet sprayer 324 protrude upwardly from the jet sprayer manifold 342 and through the lower grid 338, the lower grid 338 permitting the free flow of fluid into the bottles when placed in register with the plurality of jet sprayers 322. Thus, jet sprayers 322 are for use in directing water upwardly into the bottles 334 and the insert basket during washing operations.

In use, water is introduced upwardly into washing chamber 332 by the jet sprayers 322 and a tall center jet sprayer 324, both of which extend from the jet sprayer manifold 342. In the preferred and depicted embodiment there are eight jet sprayers 322 and one tall center jet sprayer 324. In one embodiment, the tall center jet sprayer 324 further comprises a fluid dispersion apparatus (now shown) for dispersing fluid from the tall center jet sprayer in a plurality of directions. In another embodiment of the invention, the fluid dispersion apparatus comprises a rotating head for dispersing fluid in a plurality of directions. The use of different jet configurations is within the scope of the present invention. Both the series of jet sprayers 322 and the tall center jet sprayer 324 serve the same function of routing water upwardly through grid 338 into the washing chamber 332. However, jet sprayers 322 have a lower profile than the center jet sprayer 324.

Washing chamber 332 further includes an accessory holder 352 at its upper most extent. The accessory holder 352 is mounted within a lid 350 and is sufficient for accommodating a variety of infant articles, including but not limited to nipples and bottle accessories. In one embodiment of the invention, the interior surface of the lid 350 is convex or domed. In use, fluid is projected upwards from the jet sprayers 322 and tall center jet sprayer 324 towards the interior surface of the lid 350, whereby the fluid is deflected by the interior surface of the lid 350 towards the accessories placed within the accessory holder. In one embodiment (FIG. 16), the accessory holder is an accessory holder 352 formed within the lid 350 and comprising a frame 353 in cooperation with the lid 350, a surface portion 354 with a plurality of openings 355 extending therethrough for receiving articles for an infant such as infant bottle accessories and nipples 356, and a central cavity 357 formed within the surface portion 354, wherein the plurality of openings 355 are positioned circumferentially about the surface portion 354 and are generally circular with protrusions 358 therein for increasing frictional contact with the articles for an infant. In another embodiment, the rounded holders may be particularly adapted to receive standard diameter nipples or other associated accessories, including but not limited to 1 inch and 1.5 inch diameter nipples. Rounded holders of varying diameter are within the scope of the present invention. In yet another embodiment of the present invention, the accessory holder 352 may include additional voids or openings to permit fluid to fall back to the base of the washing chamber after encountering the domed interior surface of the second lid 350.

Figure 19:
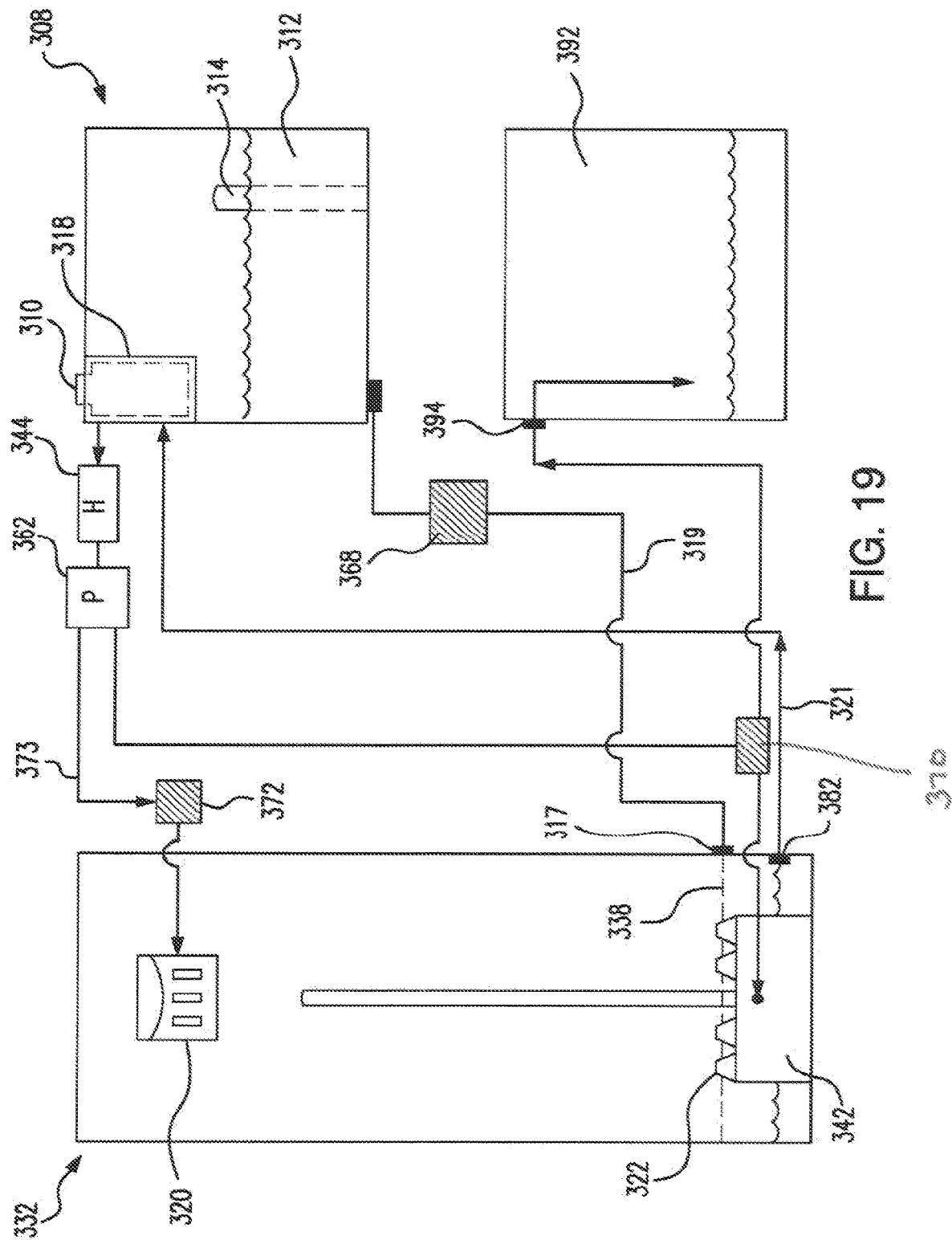
FIG. 19 is a flow diagram depicting a fluid flow path of the second alternative embodiment of the washing apparatus.

With reference to FIG. 19, apparatus 300 further includes a first solenoid valve 368, a second solenoid valve 370, and a third solenoid valve 372 for controlling the flow path of associated fluid. First solenoid valve 368 is preferably a two-way solenoid valve that controls the flow of fluid from the rinse water container 312 to the washing chamber 332. Second solenoid valve 370 is preferably a three-way solenoid valve positioned downstream of pump 362 and controlling the flow of fluid leaving the wash chamber by either directing the fluid to the jet sprayer manifold 342 or to the waste water container 392. Third solenoid valve 372 is preferably a two-way solenoid valve and is also positioned downstream pump 362 and upstream of detergent basket 320, thereby controlling the flow of rinse water from the pump 362 through a detergent line 373 to the detergent basket 320.

In a preferred embodiment, the apparatus 300 includes an internal recirculation line 321 comprising a second solenoid valve 370, a heating element 344, and a pump 362, the internal recirculation line 321 in communication with the washing chamber 332, the filter chamber 318, and the jet sprayer manifold 342, the second solenoid valve 370 having a first orientation and a second orientation, wherein in the first orientation the pump 362 directs the rinse water from the washing chamber 332 through the filter chamber 318 to the jet sprayer manifold 342, and wherein in the second orientation the pump 362 directs the rinse water from the washing chamber 332 through the filter chamber to the waste water reservoir 392.

Waste water container 392 is adapted to fit within the opening 328 of housing 302 for receiving waste water from the washing chamber 332. The waste water is collected into the waste water container 392 through a series of waste water inlet ports 394 that are coupled to outlet ports, including those as substantially as described in the aforementioned embodiments. Thereafter once wash and rinse cycle operations are complete the waste water container 392 can be removed from housing 302 and the water drained by way of port 396. Additionally waste water container 392 includes a male latch that is adapted to cooperate with a female latch upon apparatus 300 that can insure that the system 300 cannot operate without the waste water container properly coupled. In the preferred embodiment, the latches can be locked together via a solenoid or latch circuit.

In a single use, apparatus 300 performs four cycles, including a pre-rinse cycle, a detergent cycle, a first rinse cycle, and a second rinse cycle. Prior to apparatus 300 being turned on, approximately six cups of water are placed in the rinse water container 312. Initially, first solenoid valve 368 is closed, preventing the rinse water in the rinse water container 312 from flowing into the washing chamber 332. Once apparatus 300 is turned on, the apparatus 300 enters the pre-rinse cycle, wherein the first solenoid valve 368 opens in a predesigned sequence, remaining open for a predetermined time sufficient to permit approximately one quarter of the total rinse water volume, or approximately 1.5 cups of water, to flow from the rinse water container 312 to the washing chamber 332. As a result of opening the first solenoid valve 368, gravity delivers water from the rinse water container 312 and into the washing chamber 332. Once the desired volume of fluid is sent to the washing chamber 332, the first solenoid valve 368 closes, preventing the flow of additional fluid to washing chamber 332.

Pump 362 is next motorized via an electric motor. Pump 362 circulates water from the base of the washing chamber 332 into a recirculation port 382 and through internal recirculation line 321, through the water filter 310, through an in-line heater 344, through the pump 362, and through the second solenoid valve 370, the second solenoid valve 370 initially configured to direct the fluid to the jet sprayer manifold 342 and into the series of jet sprayers 322 and the tall center jet sprayer 324. Once the rinse water is delivered from the sprayers (322, 324) it encounters the bottles and the various accessories positioned within the washing chamber before returning to the base of the washing chamber, where it is again driven through a recirculation inlet port and is recirculated through the apparatus 300. During recirculation, pump 362 again operates to take up the recirculated water and deliver it back out to jet sprayers 322 and tall center jet sprayer 324 as described. The rinse water is recirculated multiple times in this fashion until it reaches an optimal temperature of approximately 150 degrees Fahrenheit. After a predetermined number of recirculation cycles, second solenoid valve 370 is reconfigured to direct the fluid to flow to the waste water container 392 prior to the start of the detergent cycle.

In the detergent cycle, first solenoid valve 368 opens for a time sufficient to permit the flow of a second 1.5 cups of water to the washing chamber 332 by gravity. Second solenoid valve 370 is returned to the configuration that permits fluid to flow into the jet sprayer manifold 342. The pump 362 then functions to drive water through the recirculation cycle. Once the optimal temperature of approximately 150 degrees Fahrenheit is achieved, third solenoid valve 372 opens, thereby permitting fluid to flow from the pump to an outlet connected to the detergent basket 320. The number of cycles needed to attain this optimal temperature can vary. Third solenoid valve 372 remains open for a predetermined time sufficient to dissolve the detergent placed in the detergent basket 320. The detergent mixes with the recirculating water and is recirculated for a predetermined time. Also, it is within the scope of the present invention to change the number of required cycles or the optimal temperature of the detergent or rinse water. Once the desired number of recirculation cycles is complete, the second solenoid valve 370 directs the water to the waste container 392.

Once the detergent cycle is complete, first solenoid valve 368 operates again to permit fluid to enter the washing chamber 332, thereby permitting the initiation of the first rinse cycle. Again, the pump 362 recirculates the water through the apparatus as described above. The first rinse cycle is then followed by a second rinse cycle.

A temperature sensor, timer, and microprocessor are included for regulating the length of the cycles. In one embodiment of the invention, the temperature sensor is a thermistor.

Breast Pump Accessory Holder

Figure 20:
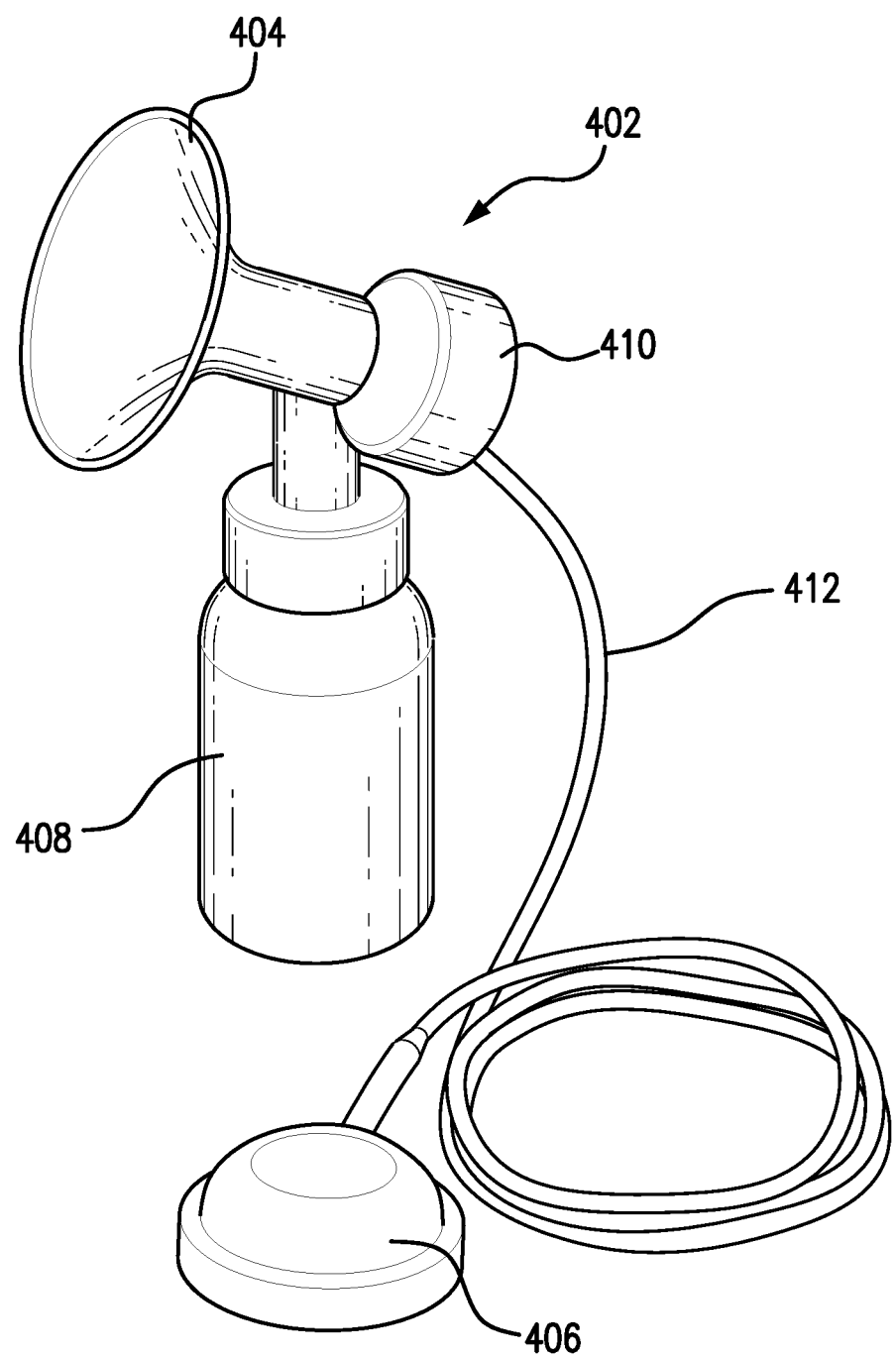
FIG. 20 is a perspective view of a breast pump assembly.
Figure 21:
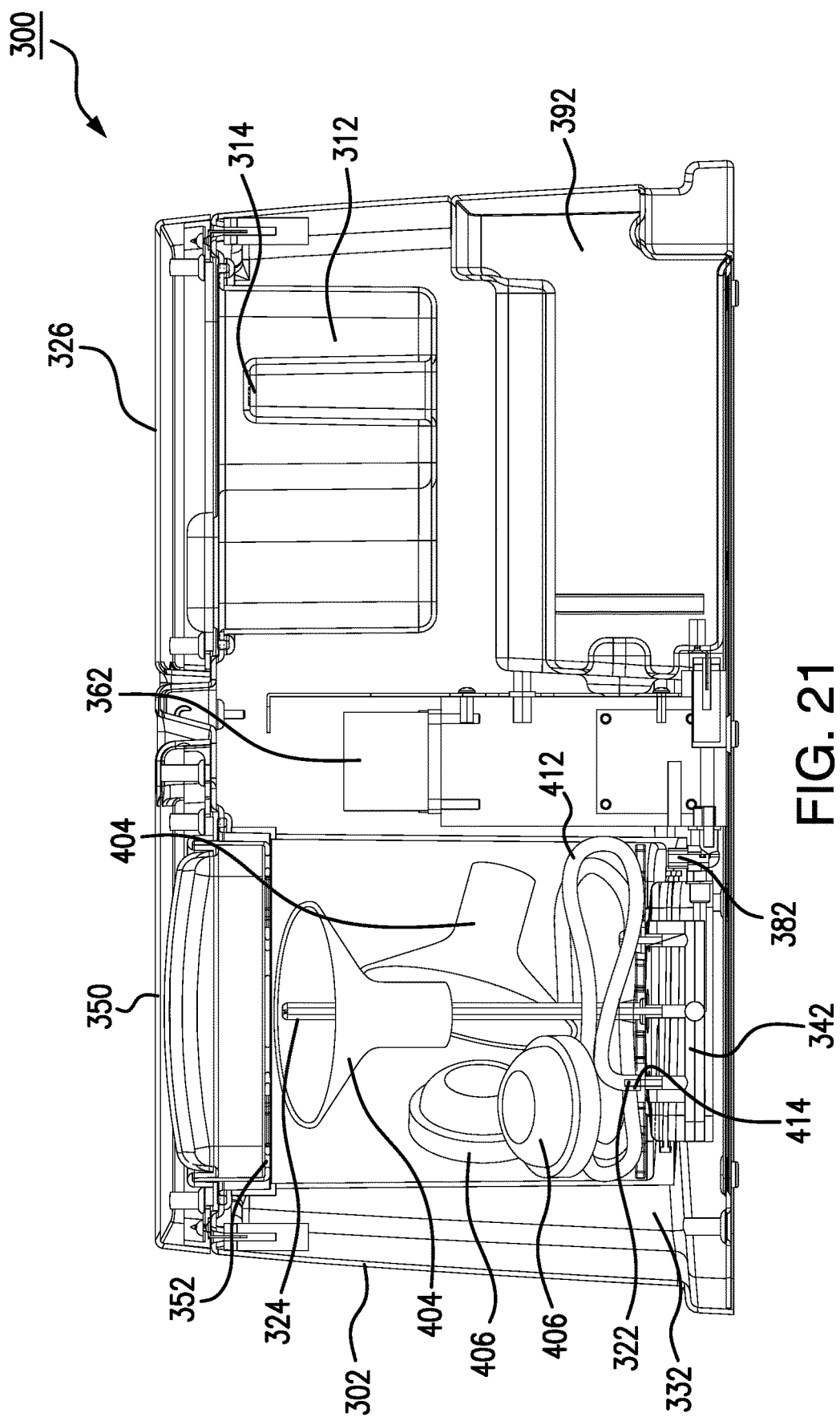
FIG. 21 is a sectional view of the breast pump accessories positioned within the apparatus.
Figure 22:
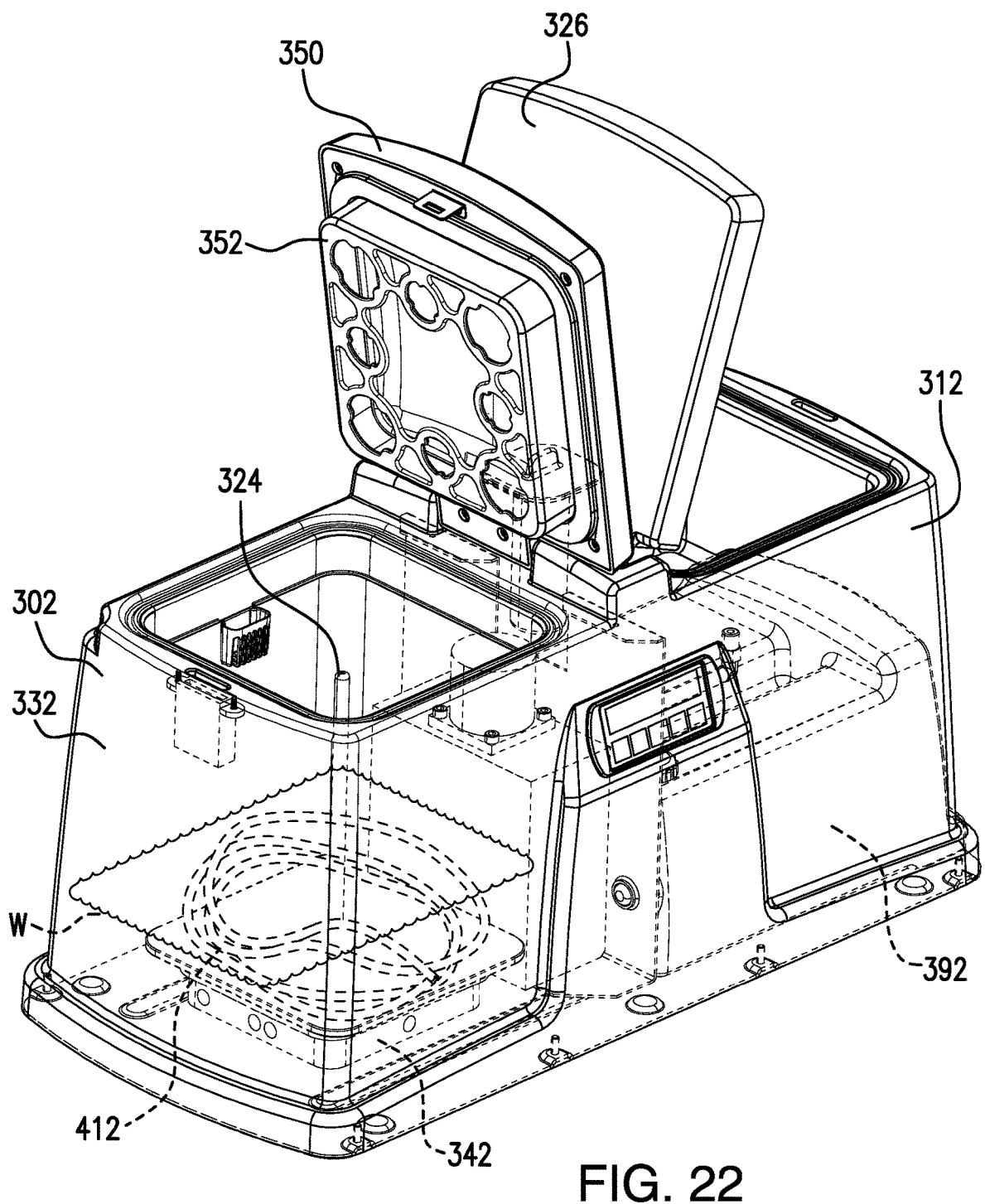
FIG. 22 is a perspective view of the breast pump accessories positioned within the apparatus.

Apparatus 300 can also be used to store, clean, and sanitize the components of a breast pump assembly 402. Breast pump assembly 402 can take any of a variety of forms. As depicted in FIG. 20, the breast pump assembly 402 includes a breast shield 404, a membrane 406, a bottle, 408, a connector 410, and a length of tubing 412. These components must be completely cleaned or sterilized after each use to ensure that the infant does not ingest germs or bacteria. However, thoroughly cleaning these individual components can prove problematic. Conventional dishwashers are too large and cleaning the breast pump accessories along with other household items is less than ideal. The other known alternative is to place the individual components into a pot of boiling water. But this is a time consuming process. In accordance with the present disclosure, and as illustrated in FIG. 21, the various components of the breast pump 402 can be cleaned within the previously described washing apparatus 300. This is accomplished by taking apart the components of breast pump assembly placing them within the washing chamber 332. Smaller components, such as the membrane 406, can be placed within the upper accessory holder 352 within lid 350. Once secured, the apparatus 300 would go through its typical wash cycle as detailed above.

One especially difficult component to clean is the tubing 412. Merely placing the tubing 412 in a conventional dishwasher does not sufficiently clean the entire internal length of tubing 412. In this regard, two methods are envisioned for using apparatus 300 to clean or sterilize the internal length of tubing 412. In one embodiment, end 414 of tubing 412 is secured over one of the jet sprayers 322. The majority of the length of tubing 412 is thereafter wrapped around manifold 342. It is also possible for tubing 412 to be wrapped around the other jet sprayers 322. In either event, it is envisioned that one end 414 would be secured over jet sprayer 322 in a fluid tight manner. Thereafter, heated water emanating from the sprayer 322 would fill and clean the entire internal length of tubing 412. If necessary, an adapter or nipple can be used to couple tubing end 414 to sprayer 322.

In another embodiment, the wash cycle is altered so that the water level W is elevated within washing chamber 322. Water level W should be high enough to entirely submerge tubing 412 in water. The wash cycle would leave the water at this level for a predetermined amount of time. Soaking tubing 412 in this manner, and for a predetermined amount of time, ensures that the entire internal length is cleaned with water. This modification to the wash cycle can be done in association with affixing the tubing end 414 to a jet sprayer 322 as described above.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A countertop apparatus for washing and sanitizing dishware comprising:
   a housing with a fluid chamber for receiving rinse water, an opening, a washing chamber for receiving items to be washed, an internal water line extending between the fluid chamber and the washing chamber, and a lid;
   a waste water reservoir positioned within the opening of the housing, the waste water reservoir receiving water from the washing chamber;
   a jet sprayer manifold within the washing chamber, the jet sprayer manifold directing fluid from the fluid chamber upwardly into the washing chamber during washing operations; and
   a plurality of jet sprayers and a center jet sprayer in fluid communication with the jet sprayer manifold;
   a lower grid for accommodating dishware to be washed, the lower grid positioned within the washing chamber and above the jet sprayer manifold, the plurality of jet sprayers and the center jet sprayer extending upwards through the lower grid.

2. The apparatus as described in claim 1, further comprising a first solenoid valve for regulating fluid flow through the internal water line.

3. The apparatus as described in claim 1, further comprising a holder for receiving the dishware.

4. The apparatus as described in claim 1, further comprising an internal recirculation line in fluid communication with the washing chamber and the jet sprayer manifold.

5. The apparatus as described in claim 4, further comprising a heating element in thermal communication with the internal recirculation line.

6. The apparatus as described in claim 2, further comprising a second solenoid valve and a pump, the second solenoid valve having a first orientation and a second orientation, wherein in the first orientation the pump directs the rinse water from the washing chamber to the jet sprayer manifold, and wherein in the second orientation the pump directs the rinse water from the washing chamber to the waste water reservoir.

7. The apparatus as described in claim 1, further comprising a detergent basket for receiving detergent, the detergent basket integrally connected to an interior wall of the washing chamber.

8. The apparatus as described in claim 7, further comprising a detergent line including a solenoid valve, the solenoid valve controlling the flow of rinse water to the detergent basket.

9. A countertop apparatus for washing and sanitizing items comprising:
   a housing with a fluid chamber for receiving rinse water, a washing chamber for receiving items to be washed, an internal water line therebetween;
   a lid pivotally attached over the washing chamber, the lid having a domed interior surface;
   a waste water reservoir positioned within an opening of the housing, the waste water reservoir receiving water from the washing chamber;
   a jet sprayer manifold within the washing chamber, the jet sprayer manifold including a number of sprayers for directing fluid upwardly into the washing chamber and against the domed interior surface of lid;
   an article holder, the article holder receiving items to be washed, the items within the holder being washed by fluid from the sprayers, and whereby fluid from the sprayers is deflected by the domed interior surface of lid to ensure adequate fluid circulation and cleaning;
   a detergent basket for receiving detergent, the detergent basket integrally connected to an interior wall of the washing chamber.

10. The apparatus as described in claim 9, further comprising a detergent line including a solenoid valve, the solenoid valve controlling the flow of rinse water to the detergent basket.

11. The apparatus as described in claim 9, further comprising an internal recirculation line in fluid communication with the washing chamber and the jet sprayer manifold.

12. The apparatus as described in claim 11, further comprising a heating element in thermal communication with the internal recirculation line.

* * * * *